(12) United States Patent
Booth

(10) Patent No.: US 8,586,634 B2
(45) Date of Patent: Nov. 19, 2013

(54) THERAPEUTIC COMPOUNDS

(75) Inventor: Raymond G. Booth, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 609 days.

(21) Appl. No.: 12/452,100

(22) PCT Filed: Jun. 13, 2008

(86) PCT No.: PCT/US2008/007458
§ 371 (c)(1),
(2), (4) Date: Aug. 15, 2010

(87) PCT Pub. No.: WO2008/156707
PCT Pub. Date: Dec. 24, 2008

(65) Prior Publication Data
US 2010/0305212 A1    Dec. 2, 2010

Related U.S. Application Data

(60) Provisional application No. 60/934,743, filed on Jun. 15, 2007, provisional application No. 61/070,386, filed on Mar. 21, 2008.

(51) Int. Cl.
*A61K 31/135* (2006.01)
*A61K 31/015* (2006.01)

(52) U.S. Cl.
USPC ............ 514/647; 514/765; 514/909; 514/929

(58) Field of Classification Search
USPC .................................. 514/647, 765, 909, 929
See application file for complete search history.

(56) References Cited

U.S. PATENT DOCUMENTS

| | | |
|---|---|---|
| 6,835,548 B2 | 12/2004 | Fong et al. |
| 7,115,767 B2 | 10/2006 | Liu et al. |
| 2003/0199690 A1 | 10/2003 | Dahanukar et al. |
| 2006/0246448 A1 | 11/2006 | Ullrich et al. |

FOREIGN PATENT DOCUMENTS

| | | |
|---|---|---|
| EP | 0230270 A2 | 7/1987 |
| EP | 0354686 A1 | 2/1990 |
| FR | 3101 M | 1/1965 |
| FR | 1480455 A | 5/1967 |
| FR | 2353519 A1 | 12/1977 |
| WO | WO-9509155 A2 | 4/1995 |
| WO | WO 03072093 A1 * | 9/2003 |
| WO | WO-2005035504 A2 | 4/2005 |
| WO | WO-2007081542 A2 | 7/2007 |

OTHER PUBLICATIONS

Nielsen et al., "Sertraline, a serotonin-uptake inhibitor, reduces food intake and body weight in lean rats and genetically obese mice", The American Journal of Clinical Nutrition, vol. 21, No. 3, pp. 185S-189S (Jan. 1992).*

Abdel-Salam et al., "Effect of Different Drugs Influencing Monoamine Neurotransmission on Haloperidol-Induced Catalepsy in Mice", Turkish Journal of Medical Sciences, vol. 37, No. 6, pp. 333-338 (2007).*

Pae et al., "Irritable bowel syndrome in psychiatric perspectives: a comprehensive review", International Journal of Clinical Practice, vol. 61, No. 10, pp. 1708-1718 (2007). Enclosed Abstract.*

Booth,R.G. et al; Novel ligands stabilize stereo-selective conformations of the histamine H1 receptor to activate catecholamine synthesis, Inflammation Research, vol. 56. No. suppl.1, Mar. 14, 2007, pp. S43-S44, XP002664944.

Ghoneim, Ola M. et al; "Novel ligands for the human histamine H1 receptor: Synthesis, pharmacology, and comparative molecular field analysis studies of 2-dimethylamino-5-(6)-phenyl-1,2,3,4-tetrahydronaphthalenes", Bioorganic & Medicinal Chemistry, vol. 14, No. 19, 2006, pp. 6640-6658, XP002664945, *abstract; compounds 4,5a-d*.

Booth, R.G., et al: "Ligand-directed multifunctional signaling of histamine H1 receptors", Inflammation Research, vol. 54, No. suppl., 2005, pp. S44-S45, XP002664946.

Moniri, N.H., et al: "Functional heterogeneity of histamine H1 receptors", Inflammation Research, vol. 53, No. suppl. 1, 2004, pp. S71-S72, XP002664947.

Gala, Dinesh et al: "Development of an Efficient Processs for the Preparation of Sch 369166: Aziridinium Chemistry on Scale", Organic Process Research & Development, vol. 8, No. 5, 2004, pp. 754-768, XP002664948, *example 5,20-23*.

Moniri, Nader H. et al: "Ligand-Directed Functional Heterogeneity of Histamine H1 Receptors: Novel Dual-Function Ligands Selectively Activate and Block H1-Mediated Phospholipase C and Adenylyl Cyclase Signaling", Journal of Pharmacology and Experimental Therapeutics, vol. 311, No. 1, 2004, pp. 274-281, XP002664949, *abstract; figure 1*.

Andrews, David R. et al: "Reaction of aziridinium ions with organometallic reagents: optimization of the key step of ecopipam synthesis", Tetrahedron Letters, vol. 43, No. 35, 2002, pp. 6121-6125, XP002664950, *examples 5a-c, 10, 12*.

Bucholtz, Ehren C. et al: "Synthesis, Evaluation, and Comparative Molecular Field Analysis of 1-Phenyl-3-amino-1,2,3,4-tetrahydronaphthalenes as Ligands for Histamine H1 Receptors", Journal of Medicinal Chemistry, vol. 42, No. 16, 1999, pp. 3041-3054, XP002664951.

Wyrick, Steven D. et al: "1-Phenyl-3-amino-1,2,3,4-tetrahydronaphthalenes and Related Derivatives as Ligands for the Neuromodulatory .o3 Receptor: Further Structure-Activity Relationships", Journal of Medicinal Chemistry, vol. 38, No. 19, 1995, pp. 3857-3864, XP002664952.

(Continued)

*Primary Examiner* — Kevin E Weddington
(74) *Attorney, Agent, or Firm* — Edwards Wildman Palmer LLP; Peter F. Corless; Jeffrey D. Hsi

(57) ABSTRACT

The invention relates to protein binding interacting/binding compounds and methods of identifying and using them. The invention further relates to pharmaceutical compositions and methods for treating 5-HT2C disorders, including diseases and disorders mediated by GPCRs.

12 Claims, 18 Drawing Sheets

(56) References Cited

OTHER PUBLICATIONS

Myers, Andrew M. et al: "Conformational Analysis, Pharmacophore Identification, and Comparative Molecular Field Analysis of Ligands for the Neuromodulatory σ3 Receptor", Journal of Medicinal Chemistry, vol. 37, No. 24, 1994, pp. 4109-4117, XP002664953.

Bertolini, G., et al: "Dopamine receptor agonists. I. Synthesis and pharmacological evaluation of 4-aryl-substituted analogs of 6,7-dihydroxy-2-amino tetralin (6,7-ADTN) and related indane compounds", European Journal of Medicinal Chemistry, vol. 27, No. 7, 1992, pp. 663-672, XP002664954, *introduction; compounds 1a-c, 2a-c, 23*.

Yamashita, Toshiaki et al: "Photoinduced Nucleophilic Addition of Ammonia and Alkylamines to Aryl-Substituted Alkenes in the Presence of p-Dicyanobenzene", Bulletin of the Chemical Society of Japan, vol. 64, No. 2, 1991, pp. 366-374, XP002664955, *compounds 14a/b, 15a/b, 16a/b*.

Kandeel, E.M. et al: "Substituted tetralins. 5. Analgesic properties of some diastereoisomeric N,N-dimethyl-4-phenyl-1,2,3,4-tetrahydro-2-naphthylamines", Journal of Medicinal Chemistry, vol. 16, No. 8, 1973, pp. 947-948, XP002664956, *examples 2a/b, 4a/b*.

Schreier, E.: Natural products inhibiting mitosis. XIV. Synthetic acid hydrazides and nitrogen mustard compounds of the podophyllotoxin series, Helvetica Chimica Acta, vol. 46, No. 7, 1963, pp. 2940-2965, XP002664957, *compounds V, XXVIII(1), XXIX(1), XXX(1), XXXI(1)*.

Govindachari, T.R. et al: "Application of the Bruckner method to the preparation of phenanthridines. III. 3,4-Benzophenanthridines", Chemische Berichte, vol. 91, 1958, pp. 2053-2060, XP002664958, p. 2056, compound (III) and line 38; p. 2057, lines 30-31; p. 2058, lines 20-21, p. 2059, lines 9-10, 35-36*.

International Search Report for PCT/US08/07458 published Dec. 24, 2008.

* cited by examiner

PATS WITH FIXED PENDANT PHENYL RING (–)-*Trans*-PAT competitive antagonism of 5-HT activation of 5-HT$_{2A}$ (–)-*Trans*-PAT inverse agonist activity at serotonin 5-HT2$_A$ receptors.

THERAPEUTIC COMPOUNDS

CROSS-REFERENCE TO RELATED APPLICATIONS

This application is the national stage application pursuant to 35 U.S.C. §371 of PCT application PCT/US2008/007458, filed Jun. 13, 2008, which claims the benefit of U.S. Provisional Application No. 60/934,743, filed Jun. 15, 2007 and U.S. Provisional Application No. 61/070,386, filed Mar. 21, 2008. The entire contents of the aforementioned applications are hereby incorporated herein by reference.

STATEMENT OF RIGHTS TO INVENTIONS MADE UNDER FEDERALLY SPONSORED RESEARCH

This work was supported in part by United States Public Health Service Grant MH068655. The government may have certain rights in the invention.

BACKGROUND OF THE INVENTION

Serotonin (5-hydroxytryptamine, 5HT) mediates a wide variety of central and peripheral psychological and physiological effects through 14 mammalian 5HT receptor subtypes that are grouped into the $5HT_1$-$5HT_7$ families (Sanders-Bush and Mayer, 2006). The $5HT_2$ family consists of the $5HT_{2A}$, $5HT_{2B}$, and $5HT_{2C}$ membrane-bound G protein-coupled receptors (GPCRs) that signal primarily through $G\alpha_q$ to activate phospholipase (PL) C and formation of inositol phosphates (IP) and diacylglycerol (DAG) second messengers (Raymond et al., 2001). The human $5HT_{2C}$ receptor (Saltzman et al., 1991) apparently is found exclusively in brain where it is widely expressed and putatively involved in several (patho)-physiological and psychological processes, including, ingestive behavior (Tecott et al., 1995), cocaine addiction (Fletcher et al., 2002; Rocha et al., 2002; Muller and Huston, 2006), sleep homeostasis (Frank et al., 2002), anxiety (Kennett et al., 1994; Sard et al., 2005; Heisler et al., 2007), depression (Tohda et al., 1989; Palvimaki et al., 1996), epilepsy (Heisler et al., 1998), Alzheimer's disease (Arjona et al., 2002; Stein et al., 2004), motor function (Heisler and Tecott, 2000; Segman et al., 2000), psychosis (Marquis et al., 2007; Siuciak et al., 2007) and response to antipsychotic drugs (Veenstra-VanderWeele et al., 2000; Reynolds et al., 2005). Thus, the importance of the $5HT_{2C}$ receptor as a pharmacotherapeutic target has been apparent for about 10 years, however, no $5HT_{2C}$-specific drugs have been developed.

One challenge regarding drug discovery targeting the $5HT_{2C}$ receptor is that this GPCR shares a transmembrane domain (TMD) sequence identity of about 80% with the $5HT_{2A}$ receptor and about 70% with the $5HT_{2B}$ receptor (Julius et al., 1988; 1990). The highly conserved TMDs and similar second messenger coupling has made development of agonist ligands selective for the $5HT_{2C}$ receptor especially difficult. Nevertheless, there is compelling evidence that activation of $5HT_{2C}$ receptors reduces food intake and leads to anti-obesity effects. For example, 5-$HT_{2C}$ knockout mice demonstrate increased feeding and obesity, and, they are resistant to the anorectic effects of d-fenfluramine (Tecott et al., 1995; Vickers et al., 1999; 2001; Heisler et al., 2002). Fenfluramine now is banned, because, although people using the drug showed weight loss due to activation of brain $5HT_{2C}$ receptors, fenfluramine also activates $5HT_{2A}$ receptors that may lead to adverse psychiatric (hallucinogenic) effects (Nichols, 2004) and $5HT_{2B}$ receptors which causes valvular heart disease (Connolly et al., 1997; Fitzgerald et al., 2000; Rothman et al., 2000; Roth, 2007) and pulmonary hypertension (Pouwels et al., 1990; Launay et al., 2002)—fatalities have resulted from the $5HT_{2B}$-mediated effects.

Although an agonist ligand truly selective for $5HT_{2C}$ vs. $5HT_{2A}$ and/or $5HT_{2B}$ receptors has not been reported until this paper, it has been possible to partially elucidate the role of brain $5HT_{2C}$ receptors to attenuate cocaine use and dependence using very selective (i.e., at least 100-fold) $5HT_{2A}$ and $5HT_{2C}$ antagonists in rat cocaine self-administration paradigms. For example, the selective $5HT_{2A}$ antagonist M100907 (Kehne et al., 1996) does not alter responding rate for cocaine self-administration but the selective $5HT_{2C}$ antagonist SB242084 (Bromidge et al., 1997) increases the rate of cocaine self-administration dose-dependently (Fletcher et al., 2002). The tremendous potential of $5HT_{2C}$ agonist pharmacotherapy for psychostimulant addiction now is widely recognized (Bubar and Cunningham, 2006).

The pharmacotherapeutic relevance of the $5HT_{2C}$ receptor in obesity and neuropsychiatric disorders such as psychostimulant addiction has stimulated intense interest by pharmaceutical companies to develop a selective $5HT_{2C}$ agonist, however, all $5HT_{2C}$ agonists reported so far also activate $5HT_{2A}$ and/or $5HT_{2B}$ receptors (Nilsson, 2006). Nevertheless, the $5HT_2$ agonist lorcaserin (APD356) recently went to Phase III clinical trials for obesity treatment even though it has only a modest 15-fold selectivity for activation of $5HT_{2C}$ receptors over $5HT_{2A}$ receptors (Jensen, 2006; Smith et al., 2006). Results reported here, however, document that a novel compound synthesized in our laboratories, (1R,3S)-(-)-trans-1-phenyl-3-dimethylamino-1,2,3,4-tetrahydronaphthalene (PAT; FIG. 1), is a full efficacy agonist at human $5HT_{2C}$ receptors, plus, it is an antagonist at $5HT_{2A}$ and $5HT_{2B}$ receptors.

G Protein-Coupled Receptors (GPCRs) can activate more than more type of G protein that results in multiple physiological/pharmacological effects, both pharmacotherapeutic and untoward side effects (Moniri et al., *Journal of Pharmacology and Experimental Therapeutics*, 311:274-281 (2004)). The phenomenon of multiple signaling pathways associated with a single GPCR can be described within the framework of the three-state model of GPCR activation, wherein, GPCRs isomerize between inactive and constitutively active states. GPCR activation causes dissociation of heterotrimeric ($\alpha$, $\beta$, $\gamma$) G protein subunits—the G$\alpha$ subunit can then activate transducer protein (e.g., PLC, AC) to alter second messenger concentration. It is now realized the same GPCR can couple to different G$\alpha$ proteins to result in "multifunctional signaling". A critical assumption of the GPCR multifunctional signaling theory is that a heterogeneity of active receptor conformations exists and that agonist ligands differ in their ability to induce, stabilize, or select among receptor conformations, as described in the "stimulus trafficking" hypothesis. It follows that, upon binding, agonist ligand chemical structural parameters are among the most important determinants of GPCR conformation that influences type of G$\alpha$ protein and signaling pathway activated.

A survey of 105 articles on the activity of 380 antagonists on 73 biological G-protein-coupled receptor targets indicates that, in this sample dataset, 322 are inverse agonists and 58 (15%) are neutral antagonists. The predominance of inverse agonism agrees with theoretical predictions which indicate that neutral antagonists are the minority species in pharmacological space (Kenakin, *Mol Pharmacol.* (2004); 65:2-11).

SUMMARY OF THE INVENTION

In one aspect, the invention provides a method of treating a subject suffering from or susceptible to a neuropsychiatric disorder comprising administering to subject in need thereof a therapeutically effective amount of a compound capable of modulating 5-HT2 binding interactions. In one embodiment, the compound is capable of agonizing a 5-HT2c. In another embodiment, the compound is capable agonizing a 5-HT2c, while antagonizing 5-HT2a and/or 5-HT2b.

In one aspect, the invention provides a method of treating a subject suffering from or susceptible to a neuropsychiatric disorder. The method includes administering to a subject in need thereof a therapeutically effective amount of a 5-HT2c agonizing compound.

In another aspect, the invention provides a method of treating a subject suffering from or susceptible to a neuropsychiatric disorder. The method includes administering to a subject in need thereof a therapeutically effective amount of a compound capable of modulating 5-HT2 binding interactions by directly modulating 5-HT2c, preferably selectively relative to 5-HT2a and/or 5-HT2b.

In another embodiment, the invention provides a method of treating a subject suffering from or susceptible to a neuropsychiatric disorder. The method includes administering to a subject identified as in need thereof a therapeutically effective amount of a 5-HT2c agonizing compound or a 5-HT2c selective compound.

In another aspect, the invention provides a method of treating a subject suffering from or susceptible to a neuropsychiatric disorder, including obesity, addiction, cocaine addiction, psychosis, anxiety, sleep homeostasis. The method includes administering to a subject agonizing 5-HT2c.

In another aspect, the invention provides a method of treating a subject suffering from or susceptible to obesity, addiction, cocaine addiction, psychosis, anxiety comprising administering to the subject an effective amount of a compound capable of agonizing 5-HT2c (including selectively relative to 5-HT2a and/or 5-HT2b), such that the subject is treated.

In one aspect, the invention provides a method of treating a subject suffering from or susceptible to a GPCR disorder comprising administering to subject in need thereof a therapeutically effective amount of a compound capable of modulating GPCR binding interactions. In one embodiment, the compound is capable of agonizing a GPCR. In another embodiment, the compound is capable antagonizing a GPCR.

In another aspect, the compounds herein are functionally selective compounds that target serotonin histamine $H_1$, $5HT_{2A, 2B, 2C}$, and acetylcholine muscarinic $M_1$-$M_5$ GPCRs. In aspects, the invention provides a method to selectively target serotonin histamine $H_1$, $5HT_{2A, 2B, 2C}$, and acetylcholine muscarinic $M_1$-$M_5$ GPCRs in a subject comprising administering to the subject a compound herein.

In another aspect, the invention provides a method of treating or preventing a GPCR-mediated disorder in a subject comprising administering to the subject identified as in need thereof a PAT compound. In certain embodiments, the PAT compound is a compound of Table 1 (infra). In certain embodiments, the PAT compound is represented by the formula (I):

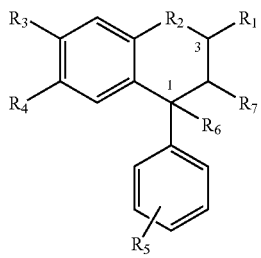

(I)
wherein,
$R_1$ is independently H, $NH_2$, NH(alkyl), N(alkyl)$_2$;
$R_2$ is independently —(CH$_2$)n-;
Each n is independently 1 or 2;

$R_3$ is independently H, OH, or halo;
$R_4$ is independently H, OH, or halo
Each $R_5$ is independently H, alkyl, or halo;
$R_6$ is independently H or alkyl; and
$R_7$ independently H, or N(alkyl)$_2$; or salt, hydrate or solvate thereof.

In certain embodiments, the PAT compound $R_1$ is —NMe$_2$. In certain embodiments, the PAT compound is (1R,3S)-(−)-Trans-1-phenyl-3-N,N-dimethylamino-1,2,3,4-tetrahydronaphthalene.

In certain embodiments, the disorder is a neuropsychiatric disorder (e.g., obesity, addiction, anxiety, depression, schizophrenia, and sleep disorders), a neurodegenerative disorder (e.g., Parkinson's Disease, Alzheimer's Disease), a neurological disorder (e.g., epilepsy), a cardiovascular disorder (e.g., hypertension), a gastrointestinal disorder (e.g., irritable bowel syndrome), or a genitor-urinary tract disorder (e.g., bladder control). In certain embodiments, the disorder is cocaine addiction. In certain embodiments, the disorder is obesity.

In another aspect, the invention provides a method of inhibiting 5-HT2C in a subject identified as in need of such treatment, comprising administering a PAT compound.

In another aspect, the invention provides a method of treating obesity in a subject, comprising administering to the subject identified as in need thereof a PAT compound capable of selectively inhibiting the 5-HT2c relative to 5-HT2a or 5-HT2b. In certain embodiments, the binding interaction for inhibiting 5-HT2c is at least 5-fold (alternatively at least 10-fold, 15-fold, 20-fold, 50-fold, 100-fold, 500 fold) greater than for either 5-HT2a or 5-HT2b. In certain embodiments, the binding interaction for inhibiting 5-HT2c is at least 100-fold greater than for either 5-HT2a or 5-HT2b.

In another aspect, the invention provides a method for identifying a compound that is capable of modulating 5-HT2c activity, comprising; (i) producing a three-dimensional representation of a molecule or molecular complex, wherein said molecule or molecular complex comprises a binding pocket defined by structure coordinates of 5-HT2c; or b) a three-dimensional representation of a homologue of said molecule or molecular complex, wherein said homologue comprises a binding pocket that has a root mean square deviation from the backbone atoms of said amino acids of not more than about 2.0 angstroms; (ii) producing a three-dimensional representation of a test compound; (iii) assessing the binding interaction of the test compound with the target. In certain embodiments, the method further comprises contacting the test compound with a 5-HT2c and measuring the binding activity of the compound.

In another aspect, the invention provides a compound represented by the formula (I):

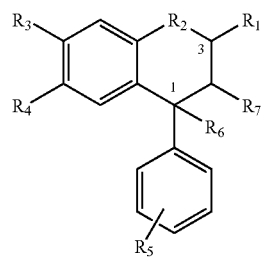

(I)
wherein,
$R_1$ is independently H, $NH_2$, NH(alkyl), N(alkyl)$_2$;
$R_2$ is independently —(CH$_2$)n-;
Each n is independently 1 or 2;

$R_3$ is independently H, OH, or halo;
$R_4$ is independently H, OH, or halo
Each $R_5$ is independently H, alkyl, or halo;
$R_6$ is independently H or alkyl; and
$R_7$ independently H, or N(alkyl)$_2$;
or salt, hydrate or solvate thereof.

In certain embodiments, the compound substituents at the 1-position and the 3-position are in the trans-orientation to one another.

In another aspect, the invention provides a composition comprising a compound described herein (e.g., a compound of Formula (I)) and a pharmaceutically acceptable carrier.

In another aspect, the invention provides a method making a composition comprising combining a compound described herein (e.g., a compound of Formula (I)) and a pharmaceutically acceptable carrier.

In another aspect, the invention provides a compound of the formula:

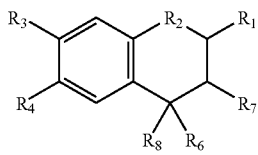

wherein,
$R_1$ is independently H, NH$_2$, NH(alkyl), N(alkyl)$_2$;
$R_2$ is independently —(CH$_2$)n-;
Each n is independently 1 or 2;
$R_3$ is independently H, OH, or halo;
$R_4$ is independently H, OH, or halo
Each $R_5$ is independently H, alkyl, or halo;
$R_6$ is independently H or alkyl;
$R_7$ independently H, N(alkyl)$_2$; and
R8 is independently aryl or heteroaryl, each optionally substituted with 1-4 independent $R_5$;
or salt, hydrate or solvate thereof.

Results of structure-activity relationship (SAR) studies indicate that affinity selectivity of the invention compounds for H$_1$ vs. 5HT$_{2A}$ vs. 5HT$_{2B}$ vs. 5HT$_{2C}$, vs, M$_1$ vs. M$_2$ vs. M$_3$ vs. M$_4$ vs. M$_5$ GPCRs is dependent on the stereochemistry of the substituents at the C1 (pendant phenyl or other aromatic) and C3 (amine) positions and, the chemical nature of the C1 and C3 substituents, as well as, the chemical substituents at the C6 and C7 positions of the tetrahydronapthalene ring system (carbon numbering as in Formula I, Table 1). Likewise, agonist vs. inverse agonist vs. antagonist activity at H$_1$ vs. 5HT$_{2A}$ vs. 5HT$_{2B}$ vs. 5HT$_{2C}$, vs, M$_1$ vs. M$_2$ vs. M$_3$ vs. M$_4$ vs. M$_5$ GPCRs is determined by the chemical nature and stereochemistry of the substituents(s) at C1, C3, C6, and C7. See, e.g., Bucholtz, E. C., Wyrick, S. D., Owens, C. E., and Booth, R. G. 1-Phenyl-3-dimethylaminotetralins (PATs): Effect of stereochemistry on binding and function at brain histamine receptors. *Medicinal Chemistry Research* 8:322-332 (1998); Bucholtz, E. C., Brown., R. L., Tropsha, A., Booth, R. G, and Wyrick, S. D. Synthesis, Evaluation and Comparative Molecular Field Analysis of 1-Phenyl-3-amino-1,2,3,4-tetrahydronaphthalenes as Ligands for Histamine H$_1$ Receptors. *Journal of Medicinal Chemistry.* 42:3041-3054 (1999); Choksi, N. Y., Nix, William B., Wyrick, S. D., and Booth, R. G. A novel phenylaminotetralin recognizes histamine H$_1$ receptors and stimulates dopamine synthesis in vivo in rat brain. *Brain Research* 852:151-160 (2000); Booth R G, Moniri N H, Bakker R A, Choksi N Y, Timmerman H, and Leurs R. A novel phenylaminotetralin radioligand reveals a sub-population of histamine H$_1$ receptors. *Journal of Pharmacology and Experimental Therapeutics* 302:328-336 (2002); Moniri N H, Covington-Strachan D, Booth R G. Ligand-directed functional heterogeneity of histamine H$_1$ receptors: Novel dual-function ligands selectively activate and block H$_1$-meditated phospholipas C and adenylyl cyclase signaling. *Journal of Pharmacology and Experimental Therapeutics,* 311:274-281 (2004); Booth R G, Moniri N H. Ligand-directed multifunctional signaling of histamine H$_1$ receptors *Inflammation Research* 54: S44-45 (2005); Ghoneim O M, Legere J A, Glbraikh A, Tropsha A, Booth R G. Novel ligands for the human histamine H$_1$ receptor: Synthesis, pharmacology, and comparative molecular field analysis studies of 2-dimethylamino-5-(6)-phenyl-1,2,3,4-tetrahydronaphthalenes. *Bioorganic and Medicinal Chemistry,* 14:6640-6658 (2006); Booth R G, Moniri N H. Novel Ligands Stabilize Stereo-Selective Conformations of the Histamine H1 Receptor to Activate Catecholamine Synthesis. *Inflammation Research* 56:1-12 (2007).

In another embodiment, the compounds herein can distinguish and selectively activate brain H$_1$ receptors that couple to the adenylyl cyclase (AC)/cAMP vs. phospholipase C (PLC)/ inositol phosphates (IP) intracellular signaling pathways to modulate brain catecholamine (dopamine, norepinephrine) neurotransmitter synthesis. In aspects, the invention provides a method of selectively activating brain H$_1$ receptors that couple to the adenylyl cyclase (AC)/cAMP vs. phospholipase C (PLC)/inositol phosphates (IP) intracellular signaling pathways to affect physiologically processes sensitive to H$_1$/AC/cAMP signaling, e.g., modulation brain catecholamine (dopamine, norepinephrine) neurotransmitter synthesis in a subject comprising administering to the subject a compound herein.

In another aspect, the compounds herein are compounds that selectively enhance H$_1$-mediated AC/cAMP signaling to treat a patient suffering from certain neuropsychiatric diseases involving altered catecholamine neurotransmission. In aspects, the invention provides a method of selectively enhancing H$_1$-mediated AC/cAMP signaling to treat a subject suffering from certain neuropsychiatric diseases involving altered catecholamine neurotransmission comprising administering to the subject a compound herein.

In another embodiment, the compounds herein are compounds that are antagonists and inverse agonists of untoward H$_1$-mediated effects that proceed via H$_1$/PLC/IP signaling, e.g., respiratory distress (bronchial constriction), diarrhea (GI contractions), and edema and hypotension (increased vascular permeability), especially associated with the peripheral allergic response. In aspects, the invention provides a method of antagonizing (e.g., blocking) untoward H$_1$-mediated effects that proceed via the PLC/IP pathway in a subject comprising administering to the subject a compound herein.

In another aspect, the PATs are antagonists as well as inverse agonists at serotonin 5HT$_{2A}$ and 5HT$_{2B}$ receptors.

In another embodiment, the PATs are antagonists as well as inverse agonists at histamine H$_1$ receptors linked to PLC/IP signaling.

In another aspect, the PATs are antagonists as well as inverse agonists at acetylcholine muscarinic M$_1$-M$_5$ receptors.

In another aspect, the PATs are antagonists as well as inverse agonists and agonists at acetylcholine muscarinic M$_1$-M$_5$ receptors. In another aspect, the PATs are simultaneously inverse agonists at serotonin 5HT$_{2A}$ and 5HT$_{2B}$ receptors and agonists at 5HT$_{2C}$ receptors. In aspects, the invention provides a method of treating or preventing a disease or disorder (e.g., psychiatric disorder; obesity) in a subject comprising administering to the subject a compound that is simultaneously an inverse agonist at serotonin $5HT_{2A}$ and $5HT_{2B}$ receptors and agonist at $5HT_{2C}$ receptors. In another embodiment, the method is that wherein the subject is in need of treatment for both a psychiatric disorder and obesity.

In one embodiment, the compounds provide methods for pharmacologically treating a disease or disorder arising from disturbances in the acetylcholine muscarinic receptor system in a subject comprising administering to the subject a compound of any of the formulae herein. The compounds of any of the formulae herein have pharmacologically-relevant affinity for muscarinic $M_1$, $M_2$, $M_3$, $M_4$, and/or $M_5$ receptors and behave functionally as agonists, inverse agonists, and/or antagonists at one or more of the muscarinic receptors.

Typical diseases or disorders (Brown and Taylor, 2006, Muscarinic Agonists and Antagonists. In: Brunton L. L., Lazo, J. S., Parker, K. L. (Eds.), Goodman and Gilman's The Pharmacological Basis of Therapeutics $11^{th}$ Edition. McGraw-Hill, New York, N.Y., pp. 183-200) that respond to modulation of the pharmacology of muscarinic $M_1$, $M_2$, $M_3$, $M_4$, and/or $M_5$ receptors include but are not limited to: disorders of the gastrointestinal tract (constipation, diarrhea, excess acid, spasticity), urinary tract (frequency of urination, lack of urination, excess urination), glaucoma, asthma, Parkinson's disease, Alzheimer's disease, various disorders involving exocrine glands (problems with sweating, tear formation, saliva formation, mucous formation), and treatment of poisoning from certain mushrooms (e.g., those containing natural muscarine derivatives).

In another aspect, the invention provides a method for identifying a compound that modulates 5-HT2c, the method comprising obtaining a crystal structure of a 5-HT2c protein or obtaining information relating to the crystal structure of a 5-HT2c protein and modeling a test compound into or on the 5-HT2c protein structure to determine whether the compound modulates the interaction of a 5-HT2c protein. In certain embodiments, the step of modeling comprises modeling or determining the ability of the compound to bind to or associate with a binding pocket defined by structure coordinates of the one or more of transmembrane domains 1-7 of 5-HT2c.

Yet another aspect of the invention is a method for identifying a compound useful to treat or prevent obesity, addiction, cocaine addiction, psychosis, anxiety. The method includes contacting a 5-HT2c complex with a test compound, and evaluating the ability of the test compound to modulate (e.g., agonize or antagonize), 5-HT2c.

Yet another aspect of the invention is a method for identifying a compound that modulates the activity of 5-HT2c, the method comprising using the atomic coordinates of the one or more of transmembrane domains 1-7 of 5-HT2c, to generate a three-dimensional structure (e.g., in silico) of a molecule comprising a binding pocket, and employing the three-dimensional structure to identify a compound that modulates the activity of the one or more of transmembrane domains 1-7 of 5-HT2c.

In another aspect, the invention provides a packaged composition including a therapeutically effective amount of a 5-HT2c agonist compound and a pharmaceutically acceptable carrier or diluent. The composition may be formulated for treating a subject suffering from or susceptible to a neuropsychiatric disorder (e.g., obesity), and packaged with instructions to treat a subject suffering from or susceptible to a neuropsychiatric disorder.

In one aspect, the invention provides a kit for treating a neuropsychiatric disorder in a subject is provided and includes a compound herein, pharmaceutically acceptable esters, salts, and prodrugs thereof, and instructions for use. In further aspects, the invention provides kits for agonizing 5-HT2c, assessing the efficacy of an anti-obesity treatment in a subject, monitoring the progress of a subject being treated with a 5-HT2c agonist, selecting a subject with a neuropsychiatric disorder for treatment with 5-HT2c agonist, and/or treating a subject suffering from or susceptible to a neuropsychiatric disorder (e.g., obesity). In certain embodiments, the invention provides: a kit for treating a neuropsychiatric disorder in a subject, the kit comprising a compound capable of modulating (e.g., agonizing) 5-HT2c agonist activity. In other aspects the compound selectively agonizes 5-HT2c relative to 5-HT2a and/or 5-HT2b. In other aspects the compound selectively antagonizes 5-HT2a and/or 5-HT2b.

In another aspect, the invention relates to a three-dimensional structure of a one or more of transmembrane domains 1-7 of 5-HT2c, each alone or combinations thereof.

Thus, the present invention provides molecules or molecular complexes that comprise either one or both of these binding pockets or homologues of either binding pocket that have similar three-dimensional shapes.

The invention also provides a pharmaceutical composition of the compounds described herein, comprising a compound capable of agonizing 5-HT2c; a compound capable of agonizing 5-HT2c selectively relative to 5-HT2a and/or 5-HT2b; a compound capable of agonizing 5-HT2c and antagonizing 5-HT2a and/or 5-HT2b; or a pharmaceutically acceptable ester, salt, or prodrug thereof, together with a pharmaceutically acceptable carrier.

In another aspect, the invention provides a machine readable storage medium which comprises the structural coordinates of a binding pocket defining the one or more of transmembrane domains 1-7 of 5-HT2c.

In another aspect, the invention provides a computer for producing a three-dimensional representation of a molecule or molecular complex, wherein said molecule or molecular complex comprises a binding pocket defined by structure coordinates of the one or more of transmembrane domains 1-7 of 5-HT2c; or b) a three-dimensional representation of a homologue of said molecule or molecular complex, wherein said homologue comprises a binding pocket that has a root mean square deviation from the backbone atoms of said amino acids of not more than about 2.0 angstroms. The computer includes: (i) a machine-readable data storage medium comprising a data storage material encoded with machine-readable data, wherein said data comprises the structure coordinates of the one or more of transmembrane domains 1-7 of 5-HT2c; (ii) a working memory for storing instructions for processing said machine-readable data; (iii) a central-processing unit coupled to said working memory and to said machine-readable data storage medium for processing said machine readable data into said three-dimensional representation; and (iv) a display coupled to said central-processing unit for displaying said three-dimensional representation.

The invention also provides methods for designing, evaluating and identifying compounds which bind to the aforementioned binding pockets. Other embodiments of the invention are disclosed infra.

BRIEF DESCRIPTION OF THE DRAWINGS

The present invention is further described below with reference to the following non-limiting examples and with reference to the following figures, in which.

DETAILED DESCRIPTION OF THE INVENTION

Figure 1:
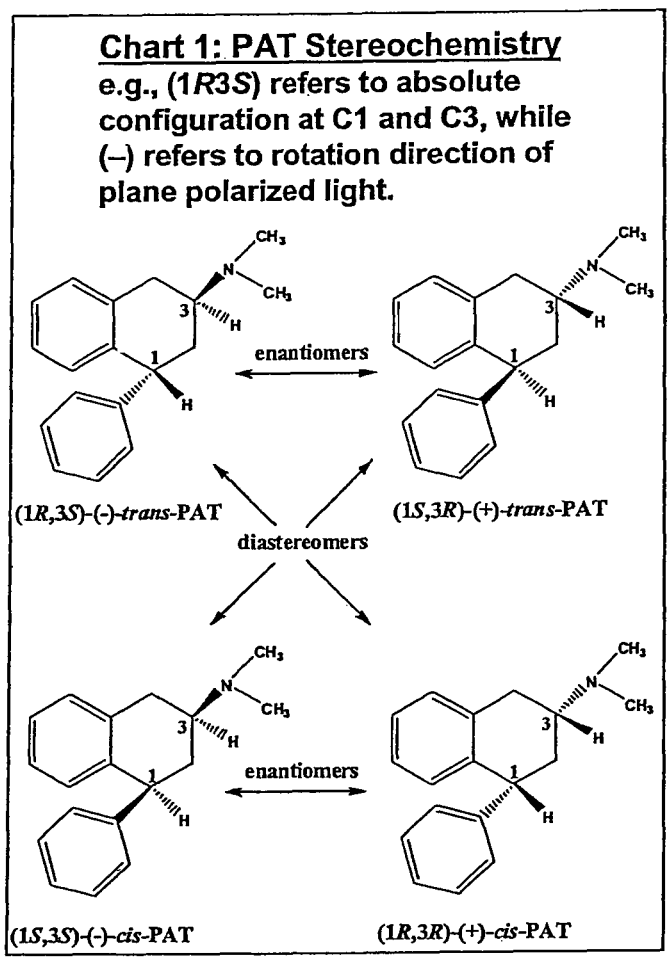
FIG. 1. depicts stereochemical relationship of cis- and trans-1-phenyl-3-dimethylamino-1,2,3,4-tetrahydronaphthalene (PAT) compounds.

The present inventors have now discovered a therapeutic strategy that addresses selective disease treatment and prevention (i.e., having reduced or minimized adverse side effects) by selectively targeting 5-HT2c. Such interactions are relevant for modulation of 5-HT2c mediated disorders, particularly in certain neuropsychiatric disorder types where 5-HT2 mechanisms play a significant role.

The present invention relates, at least in part, to the discovery that the 5-HT2c interactions are useful as targets (e.g., selective) for neuropsychiatric disorder therapy.

1. DEFINITIONS

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The term alkyl further includes alkyl groups, which can further include oxygen, nitrogen, sulfur or phosphorus atoms replacing one or more carbons of the hydrocarbon backbone, e.g., oxygen, nitrogen, sulfur or phosphorus atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl (benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a disorder delineated herein. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate."

The term "haloalkyl" is intended to include alkyl groups as defined above that are mono-, di- or polysubstituted by halogen, e.g., fluoromethyl and trifluoromethyl.

The terms "halogen" and "halo" designate —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "GPCR disorder" includes any disease, disorder or symptoms thereof that are mediated by a G protein-coupled receptor (e.g., 5-HT2a, 5-HT2b, 5-HT2c, muscarinic M1-M5). Diseases and disorders mediated by such GPCRs include, for example, neuropsychiatric disorders (e.g., obesity, addiction, cocaine addiction, psychosis anxiety, depression, schizophrenia, psychosis, and sleep disorders), neurodegenerative disorders (e.g., Parkinson's Disease, Alzheimer's Disease), neurological disorders (e.g., epilepsy), cardiovascular disorders (e.g., hypertension), gastrointestinal disorders (e.g., irritable bowel syndrome), and genitor-urinary tract disorders (e.g., bladder control).

The language "M1-M5 GPCR" refers to the cholinergic muscarinic M1-M5 neurotransmitter G protein-coupled receptors (including those delineated herein) that.

The language "5-HT2" refers to the serotonin receptors (including those delineated herein) such as 5-HT2a, 5-HT2b and 5-HT2c sub-types.

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-(C1-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a compound inhibit activity of a target in response to exposure to a compound of the invention, including for example in an subject (e.g., animal, human) such that a desired end result is achieved, e.g., a therapeutic result.

The term "obtaining" as in "obtaining a compound capable of modulating (agonizing, antagonizing) a target delineated herein and is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a disorder herein.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a disorder herein or who could otherwise benefit from the administration of a compound of the invention, such as human and non-human animals. Preferred humans include human patients suffering from or prone to suffering from a neuropsychiatric disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a neuropsychiatric disorder" is meant to include subjects at risk of developing a neuropsychiatric disorder, e.g., including those delineated herein, i.e., subjects suffering from a neuropsychiatric disorder or symptom thereof, subjects having a family or medical history of neuropsychiatric disorder or symptom thereof, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose administration to the patient, treating or preventing a neuropsychiatric disorder and/or symptoms of a neuropsychiatric disorder, or in prolonging the survivability of the patient with such a neuropsychiatric disorder beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. COMPOUNDS OF THE INVENTION

In one aspect, the invention provides compounds capable of modulating (e.g., inhibiting or stimulating) (directly or indirectly) 5-HT binding activity.

In one embodiment, the invention provides a compound capable of agonizing 5-HT2c; and pharmaceutically acceptable esters, salts, and prodrugs thereof. In certain embodiments, the compound is a compound of Formula (I).

Certain preferred compounds include compounds specifically delineated herein:

TABLE 1

Compounds:                                                            Formula I

Configuration is stereochemistry at C1 & C3

| PAT # | Config | $R_1$ | $R_2$ | $R_3$ | $R_4$ | $R_5$ | $R_6$ | $R_7$ |
|---|---|---|---|---|---|---|---|---|
| 1 | (1R,3S)-(−)-trans | $N(CH_3)_2$ | $CH_2$ | H | H | H | H | H |
| 2 | (1S,3R)-(+)-trans | $N(CH_3)_2$ | $CH_2$ | H | H | H | H | H |
| 3 | (1R,3R)-(−)-cis | $N(CH_3)_2$ | $CH_2$ | H | H | H | H | H |
| 4 | (1S,3S)-(+)-cis | $N(CH_3)_2$ | $CH_2$ | H | H | H | H | H |
| 5 | (±)-trans (PAB) | $N(CH_3)_2$ | $(CH_2)_2$ | H | H | H | H | H |
| 6 | (±)-cis (PAB) | $N(CH_3)_2$ | $(CH_2)_2$ | H | H | H | H | H |
| 7 | (±)-trans | $N(CH_3)_2$ | $CH_2$ | Cl | OH | H | H | H |
| 8 | (±)-cis | $N(CH_3)_2$ | $CH_2$ | Cl | OH | H | H | H |
| 9 | (±)-trans | $N(CH_3)_2$ | $CH_2$ | OH | OH | H | H | H |
| 10 | (±)-cis | $N(CH_3)_2$ | $CH_2$ | OH | OH | H | H | H |
| 11 | (±)-trans | $N(CH_3)_2$ | $CH_2$ | H | H | H | $CH_3$ | H |
| 12 | (±)-cis | $N(CH_3)_2$ | $CH_2$ | H | H | H | $CH_3$ | H |
| 13 | (±)-trans | $N(CH_3)_2$ | $CH_2$ | H | H | p-Cl | H | H |
| 14 | (±)-trans | $N(CH_3)_2$ | $CH_2$ | H | H | p-F | H | H |
| 15 | (±)-trans | $N(CH_3)_2$ | $CH_2$ | H | H | $pCH_3$ | H | H |
| 16 | (±)-trans | $N(CH_3)_2$ | $CH_2$ | H | H | o-Cl | H | H |
| 17 | (±)-trans | $N(CH_3)_2$ | $CH_2$ | H | H | $oCH_3$ | H | H |
| 18 | (±)-trans | $N(CH_3)_3$ | $CH_2$ | H | H | H | H | H |
| 19 | (±)-cis | $N(CH_3)_3$ | $CH_2$ | H | H | H | H | H |
| 20 | (±)-trans | $NH(CH_3)$ | $CH_2$ | H | H | H | H | H |
| 21 | (±)-cis | $NH(CH_3)$ | $CH_2$ | H | H | H | H | H |
| 22 | (±)-trans | $NH_2$ | $CH_2$ | H | H | H | H | H |
| 23 | (±)-cis | $NH_2$ | $CH_2$ | H | H | H | H | H |
| 24 | (±)-trans | $NH_2$ | $CH_2$ | OH | OH | H | H | H |
| 25 | (±)-cis | $NH_2$ | $CH_2$ | OH | OH | H | H | H |
| 26 | (±)-trans | H | $CH_2$ | H | H | H | H | $N(CH_3)$ |
| 27 | (±)cis | H | $CH_2$ | H | H | H | H | $N(CH_3)$ |
| 28 | (±)-trans | $N(C_2H_5)_2$ | $CH_2$ | H | H | H | H | H |
| 29 | (±)-trans | $N(C_3H_5)_2$ | $CH_2$ | H | H | H | H | H |
| 30 | (±)-trans | $NCH_3(C_3H_5)$ | $CH_2$ | H | H | H | H | H |
| 31 | (±)-trans | $NH(C_3H_5)$ | $CH_2$ | H | H | H | H | H |

Synthesis of New PAT Analogs with Changes to the C(1) Pendant Phenyl Substituent Based on binding, function, 3D QSAR, and molecular modeling results in Preliminary Data, we demonstrate that the (−)-trans-PAT C(1) pendant phenyl moiety is critical to providing full-efficacy $5HT_{2C}$ agonist activity without activation of $5HT_{2A}$ and $5HT_{2B}$ receptors. Testing PAT pendant phenyl ring substitution and orientation will help to determine optimal steric and electrostatic binding interactions with $5HT_2$ active site amino acids to obtain $5HT_{2C}$ agonists and/or $5HT_{2A}/5HT_{2B}$ antagonists with higher affinity, potency, and/or selectivity.

TABLE 2

Compounds

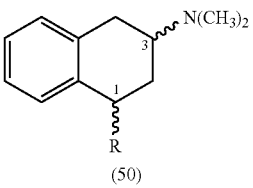

(50)

(±)-cis- & (±)-trans-

Chart of New C(1) Substituted PAT Analogs

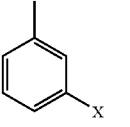

The invention also relates to the pharmaceutically acceptable salts and esters of the above-mentioned compounds.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

According to another embodiment, the invention provides compounds which associate with or bind to GPCR or binding pocket thereof produced or identified by the methods described herein.

3. USES OF THE COMPOUNDS OF THE INVENTION

In one embodiment, the invention provides methods for treating a subject for a GPCR-mediated disorder, by administering to the subject an effective amount of a compound capable of modulating (agonizing, antagonizing) a GPCR target. A GPCR disorder includes diseases and disorders mediated by such GPCRs. The herein delineated compounds, compositions and methods are useful for treating or preventing disorder including, for example, neuropsychiatric disorders (e.g., obesity, addiction, anxiety, depression, schizophrenia, and sleep disorders), neurodegenerative disorders (e.g., Parkinson's Disease, Alzheimer's Disease), neurological disorders (e.g., epilepsy), cardiovascular disorders (e.g., 5-HT2b mediated disease, hypertension), gastrointestinal disorders (e.g., irritable bowel syndrome), and genitor-urinary tract disorders (e.g., bladder control). In certain embodiments, the subject is a mammal, e.g., a primate, e.g., a human.

In one embodiment, the invention provides compounds and methods for treating a subject for a histamine (e.g., H1, H2, H3, H4)-mediated disorder, by administering to the subject an effective amount of a compound capable of modulating (agonizing, antagonizing) a histamine target. A histamine disorder includes diseases and disorders mediated by such histamine (e.g., H1). The herein delineated compounds, compositions and methods are useful for treating or preventing disorder including, for example, respiratory distress (e.g., bronchial constriction), diarrhea (GI contractions), edema, and hypotension (e.g., increased vascular permeability), allergic response, and neuropsychiatric, neurodegenerative and neurological disorders herein.

In this embodiment, the compounds of the invention may either directly or indirectly modulate (e.g., agonize, stimulate) the activity of 5-HT2c or specific domains thereof. A cell can be contacted with a compound of the invention to agonize 5-HT2c and modulate 5-HT2c mediated activity. Contacting cells or administering the compounds of the invention to a subject is one method of treating a cell or a subject suffering from or susceptible to unwanted or undesired 5-HT2C mediated activity or a 5-HT2c mediated disorder.

In one embodiment, a method of treating a subject suffering from or susceptible to a 5-HT2c disorder includes administering to a subject in need thereof a therapeutically effective amount of a compound capable of directly or indirectly modulating the activity of 5-HT2c, to thereby treat the subject. Exemplary compounds include those compounds described herein (e.g., PAT, etc.).

Thus, in one embodiment, the invention provides methods for treating a subject for a 5-HT2C disorder, by administering to the subject an effective amount of a compound capable of agonizing 5-HT2c.

In certain embodiments, the methods of the invention include administering to a subject a therapeutically effective amount of a compound of the invention in combination with another pharmaceutically active compound. Other pharmaceutically active compounds that may be used can be found in *Harrison's Principles of Internal Medicine*, Thirteenth Edition, Eds. T. R. Harrison et al. McGraw-Hill N.Y., N.Y.; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In certain embodiments, the compound of the invention can be used in combination therapy with conventional anti-obesity, (e.g., fat absorption blockers). Certain 5-HT drugs (e.g., 5-HTa or 5-HTb antagonists) have an undesirable side effect profile that tend to make them less then optimal or unsuitable for certain patients, that is, they demonstrate cardiovascular (e.g., valvular heart disease, pulmonary hypertension, cardiotoxicity) or psychiatric undesirable and or life threatening side effect profiles.

Determination of a therapeutically effective amount or a prophylactically effective amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective amount or dose, and the prophylactically effective amount or dose, a number of factors are considered by the attending clinician, including, but not limited to: the specific 5-HT2c disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective amount of a compound of the invention of the invention is expected to vary from about 0.1 milligram per kilogram of body weight per day (mg/kg/day) to about 100 mg/kg/day.

Compounds determined to be effective for the prevention or treatment of 5-HT2c disorders in animals, e.g., dogs, chickens, and rodents, may also be useful in treatment of 5-HT2c disorders in humans. Those skilled in the art of treating 5-HT2c disease in humans will know, based upon the data obtained in animal studies, the dosage and route of administration of the compound to humans. In general, the dosage and route of administration in humans is expected to be similar to that in animals.

The identification of those patients who are in need of prophylactic treatment for 5-HT2C disorders is well within the ability and knowledge of one skilled in the art. Certain of the methods for identification of patients which are at risk of developing 5-HT2C disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a 5-HT2C disorder by methods well known in the art (e.g., determining level of markers for the 5-HT2C disorder) and then administering a therapeutically effective amount of a compound delineated herein according to the invention to the subject. After an appropriate period of time after the administration of the compound (e.g., 1 day, 1 week, 2 weeks, one month, six months), the extent of the 5-HT2C disorder is determined again. The modulation (e.g., decrease) of the extent or invasiveness of the 5-HT2C disorder indicates efficacy of the treatment. The extent or invasiveness of the 5-HT2C disorder may be determined periodically throughout treatment. For example, the extent or invasiveness of the 5-HT2C disorder may be checked every few hours, days or weeks to assess the further efficacy of the treatment. A decrease in extent or invasiveness of the 5-HT2C disorder indicates that the treatment is efficacious. The method described may be used to screen or select patients that may benefit from treatment with a modulating compound of a 5-HT2C disorder.

As used herein, "obtaining a biological sample from a subject," includes obtaining a sample for use in the methods described herein. A biological sample is described above.

Yet another aspect presents a method to identify a compound that modulates the interaction of 5-HT2C or specific domains thereof. The method may include obtaining the crystal structure of 5-HT2C or specific domains thereof (optionally apo form or complexed) or obtaining the information relating to the crystal structure of 5-HT2C or specific domains thereof (optionally apo form or complexed), in the presence and/or absence of the test compound. Compounds may then be computer modeled into or on the 5-HT2C structure, or specific domains thereof (e.g., a binding site of the crystal structure) to predict stabilization of the interaction between the 5-HT2C or specific domains thereof and the test compound. Once potential modulating compounds are identified, the compounds may be screened using cellular assays, such as the ones identified herein and competition assays known in the art. Compounds identified in this manner are useful as therapeutic agents.

In another aspect, a compound of the invention is packaged in a therapeutically effective amount with a pharmaceutically acceptable carrier or diluent. The composition may be formulated for treating a subject suffering from or susceptible to a 5-HT2C disorder, and packaged with instructions to treat a subject suffering from or susceptible to a 5-HT2C disorder.

In another aspect, the invention provides methods for modulating 5-HT2C disease. In one embodiment, a method of modulating 5-HT2C (or a 5-HT2C disorder) according to the invention includes contacting cells with a compound capable of modulating 5-HT2C (or a 5-HT2C disorder), or specific domains thereof. In either embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a 5-HT2C disorder in a subject include administering an effective amount of a compound of the invention (i.e., a compound described herein) to the subject. The administration may be by any route of administering known in the pharmaceutical arts. The subject may have a 5-HT2C disorder, may be at risk of developing a 5-HT2C disorder, or may need prophylactic treatment prior to anticipated or unanticipated exposure to a conditions capable of increasing susceptibility to a 5-HT2C disorder.

In one aspect, a method of monitoring the progress of a subject being treated with a compound herein includes determining the pre-treatment status (e.g., progression, target profile, Marker profile) of the 5-HT2C disorder, administering a therapeutically effective amount of a compound herein to the subject, and determining the status (e.g., progression, target profile, Marker profile) of the 5-HT2C disorder after an initial period of treatment with the compound, wherein the modulation of the status indicates efficacy of the treatment.

The subject may be at risk of a 5-HT2C disorder, may be exhibiting symptoms of a 5-HT2C disorder, may be susceptible to a 5-HT2C disorder and/or may have been diagnosed with a 5-HT2C disorder.

If the modulation of the status indicates that the subject may have a favorable clinical response to the treatment, the subject may be treated with the compound. For example, the subject can be administered therapeutically effective dose or doses of the compound.

In another aspect, methods for evaluating a test compound comprise contacting a 5-HT2C or specific domains thereof with a test compound (complex), and evaluating the binding interaction following contact, wherein a change in the stability of the complex relative to a reference value is an indication that the test compound modulates the stability of the complex.

The 5-HT2C or specific domains thereof complex may be modeled in silico, or may be a complex within a cell, isolated from a cell, recombinantly expressed, purified or isolated from a cell or recombinant expression system or partially purified or isolated from a cell or recombinant expression system.

Kits of the invention include kits for treating a 5-HT2C disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a 5-HT2C disorder may be packaged with a kit for monitoring the progress of a subject being treated for a 5-HT2C disorder according to the invention.

The present methods can be performed on cells in culture, e.g. in vitro or ex vivo, or on cells present in an animal subject, e.g., in vivo. Compounds of the inventions can be initially tested in vitro using primary cultures of cells, e.g., transformed cells, and the like.

The present method can be performed on cells in culture, e.g. in vitro or ex vivo, or on cells present in an animal subject, e.g., in vivo. Compound of the invention can be initially tested in vitro using cells from the respiratory tract from embryonic rodent pups (See e.g. U.S. Pat. No. 5,179,109—fetal rat tissue culture), or other mammalian (See e.g. U.S. Pat. No. 5,089,517—fetal mouse tissue culture) or non-mammalian animal models.

Alternatively, the effects of compound of the invention can be characterized in vivo using animals models.

4. PHARMACEUTICAL COMPOSITIONS

The invention also provides a pharmaceutical composition, comprising an effective amount of a compound of the and a pharmaceutically acceptable carrier. In a further embodiment, the effective amount is effective to treat a 5-HT2C disorder, as described previously.

In an embodiment, the compound of the invention is administered to the subject using a pharmaceutically-acceptable formulation, e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt;

(6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

6. SCREENING METHODS AND SYSTEMS

In another aspect, the invention provides a machine readable storage medium which comprises the structural coordinates of either one or both of the binding pockets identified herein, or similarly shaped, homologous binding pockets. Such storage medium encoded with these data are capable of displaying a three-dimensional graphical representation of a molecule or molecular complex which comprises such binding pockets on a computer screen or similar viewing device.

The invention also provides methods for designing, evaluating and identifying compounds which bind to the aforementioned binding pockets. Thus, the computer produces a three-dimensional graphical structure of a molecule or a molecular complex which comprises a binding pocket.

In another embodiment, the invention provides a computer for producing a three-dimensional representation of a molecule or molecular complex defined by structure coordinates of 5-HT2C or domains thereof, or a three-dimensional representation of a homologue of said molecule or molecular complex, wherein said homologue comprises a binding pocket that has a root mean square deviation from the backbone atoms of said amino acids of not more than 2.0 (more preferably not more than 1.5) angstroms In exemplary embodiments, the computer or computer system can include components which are conventional in the art, e.g., as disclosed in U.S. Pat. Nos. 5,978,740 and/or 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket may be used for a variety of purposes, such as drug discovery.

For example, the structure encoded by the data may be computationally evaluated for its ability to associate with chemical entities. Chemical entities that associate with a binding pocket of a 5-HT2C or specific domains thereof, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket of 5-HT2C or specific domains thereof, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:

i) employing computational means to perform a fitting operation between the chemical entity and a binding pocket of the molecule or molecular complex; and ii) analyzing the results of the fitting operation to quantify the association between the chemical entity and the binding pocket. The term "chemical entity", as used herein, refers to chemical compounds, complexes of at least two chemical compounds, and fragments of such compounds or complexes.

The design of compounds that bind to 5-HT2C or specific domains thereof binding pockets according to this invention generally involves consideration of several factors. First, the entity must be capable of physically and structurally associating with parts or all of the 5-HT2C or specific domains thereof-related binding pockets. Non-covalent molecular interactions important in this association include hydrogen bonding, van der Waals interactions, hydrophobic interactions and electrostatic interactions. Second, the entity must be able to assume a conformation that allows it to associate with the 5-HT2C, or specific domains thereof, binding pocket(s) directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the binding pocket or homologues thereof.

The potential binding effect of a chemical entity on a 5-HT2C or specific domains thereof may be analyzed prior to its actual synthesis and testing by the use of computer modeling techniques. If the theoretical structure of the given entity suggests insufficient interaction and association between it and the target binding pocket, testing of the entity is obviated. However, if computer modeling indicates a strong interaction, the molecule may then be synthesized and tested for its ability to bind to a binding pocket. This may be achieved, e.g., by testing the ability of the molecule modulate 5-HT2C, or specific domains thereof, binding activity, e.g., using assays described herein or known in the art. In this manner, synthesis of inoperative compounds may be avoided.

A potential binder of 5-HT2C or specific domains thereof (e.g., binding pocket) may be computationally evaluated by means of a series of steps in which chemical entities or fragments are screened and selected for their ability to associate with the 5-HT2C or specific domains thereof-related binding pockets.

One skilled in the art may use one of several methods to screen chemical entities or fragments for their ability to associate with a 5-HT2C or specific domains thereof-related binding pocket. This process may begin by visual inspection of, for example, 5-HT2C or specific domains thereof-related binding pocket on the computer screen based on the 5-HT2C, or specific domains thereof structure coordinates described herein, or other coordinates which define a similar shape generated from the machine-readable storage medium. Selected fragments or chemical entities may then be positioned in a variety of orientations, or docked, within that binding pocket as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable interacting/binding compound chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding pocket.

Instead of proceeding to build an of a binding pocket in a step-wise fashion one fragment or chemical entity at a time as described above, interacting or other binding compounds may be designed as a whole or "de novo" using either an empty binding site or optionally including some portion(s) of a known interacting/binding compound(s). There are many de novo ligand design methods known in the art, some of which are commercially available (e.g., LeapFrog, available from Tripos Associates, St. Louis, Mo.).

Other molecular modeling techniques may also be employed in accordance with this invention [see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)].

Once a compound has been designed or selected, the efficiency with which that entity may bind to a binding pocket may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein. Many thousands of compounds can be rapidly screened and the best virtual compounds can be selected for further screening (e.g., by synthesis and in vitro testing). Small molecule databases can be screened for chemical entities or compounds that can bind, in whole or in part, to a GPCR, 5-HT2c, or specific domains thereof In this screening, the quality of fit of such entities to the binding site may be judged either by shape complementarity or by estimated interaction energy.

The compounds herein are also advantageous in that they possess a higher level of structural rigidity relative to previously reported 5-HT2 active compounds. This advantage is useful for probing structural information about GPCR targets (e.g., histamine, serotonin, muscarinic, etc.) and sub-families thereof. Such information is useful in elucidating binding pocket information, homology, sequence, etc. Thus, in aspects, the invention includes the use of the compounds delineated herein as probes for elucidation of target structure information. The use includes methods for studying interaction and function of the compounds herein with a PGCR target (both using "wet lab" experimental assays, probes, crystallization techniques and protocols, protein studies, as well as in silico methods using representations of the compounds).

EXAMPLES

The invention is further illustrated by the following examples which are intended to illustrate but not limit the scope of the invention.

Example 1

Database of Small Molecules

The NCI/DTP maintains a repository of approximately 240,000 samples (i.e., the plated compound set) which are non-proprietary and offered to the research community for discovery and development of new agents for the treatment of cancer, AIDS, or opportunistic infections afflicting subjects with cancer or AIDS. The three-dimensional coordinates for the NCI/DTP plated compound set is obtained in the MDL SD format (http://www.chm.tu-dresden.de/edv/vamp65/RE-FERS/vr_03d.htm) and converted to the mol2 format by the DOCK utility program SDF2MOL2. Partial atomic charges, solvation energies and van der Waals parameters for the ligands are calculated using SYBDB and added to the plated compound set mol2 files.

Example 2

Database Screening to Identify Potential Small Molecule Interacting/Binding Compounds In lieu of conducting high-throughput screening, a more rapid and economical structure-based approach combining molecular docking in silico with functional testing is used. A large chemical library of compounds with known three-dimensional structure is positioned in the structural pocket selected by SPHGEN (UCSF) on the crystal structure of a GPCR. This approach combines resources available through the NCI/DTP (atomic coordinates and small molecules) with improved molecular docking and scoring algorithms imposed in DOCK5.1 (UCSF). 20,000 small molecule compounds with drug-like characteristics (following the Lipinski rules) were docked into the 5-HT2c crystal structure in 100 different orientations using DOCK5.1. The compounds with the highest scores are requested for functional testing from the NCI/DTP.

The National Cancer Institute/Developmental Therapeutics Program (NCI/DTP) maintains a repository of approximately 220,000 samples (the plated compound set) that are nonproprietary and offered to the extramural research community free of charge. The three-dimensional coordinates for the NCI/DTP plated compound set was obtained in the MDL SD format and converted to the mol2 format by the DOCK utility program SDF2MOL2. Partial atomic charges, solvation energies, and van der Waals parameters for the ligands were calculated using SYBDB and added to the plated compound set mol2 file.

In Silico Molecular Docking of Potential Small Molecule Interacting/Binding Compounds.

All docking calculations are performed with the DOCK, v5.1.0. The general features of DOCK include rigid orienting of ligands to receptor spheres, AMBER energy scoring, GB/SA solvation scoring, contact scoring, internal non-bonded energy scoring, ligand flexibility, and both rigid and torsional simplex minimization. Unlike previously distributed versions, this release incorporates automated matching, internal energy (used in flexible docking), scoring function hierarchy, and new minimizer termination criteria. The coordinates for the molecular model of the 5-HT2c domain are used in the molecular docking calculations. To prepare the site for docking, all water molecules are removed. Protonation of receptor residues is performed with Sybyl (Tripos, St. Louis, Mo.). The structure is explored using sets of spheres to describe potential binding pockets. The number of orientations per molecule is 100. Intermolecular AMBER energy scoring (vdw+columbic), contact scoring, and bump filtering are implemented in DOCK5.1.0. SETOR and GRASP are used to generate molecular graphic images.

As shown herein, representative compounds herein have GPCR modulating activity.

Example 3

Chemicals (1R,3S)-(−)-Trans-1-phenyl-3-N,N-dimethylamino-1,2,3,4-tetrahydronaphthalene (trans-PAT, FIG. 1) was synthesized by modification of a procedure previously reported (Wyrick et al., 1993). Briefly, (E)-1,4-diphenylbut-1-en-3-one was cyclized to the corresponding tetralone intermediate using polyphosphoric acid in toluene under reflux conditions (18 h) and the product was purified by flash column chromatography. The tetralone was reduced with sodium borohydride to a mixture of (±)-cis- and (±)-trans-tetralols that could be separated by recrystallization. The (±)-cis-tetralol was stirred with p-toluenesulfonyl chloride in pyridine for 2 days at room temp to obtain the corresponding tosylate intermediate. Stirring the tosylate with sodium azide in N,N-dimethylformamide for 2 days at room temp yielded the (±)-trans-azido derivative, which was reduced by catalytic hydrogenation to the free amine. The (±)-trans-amine compound was converted to a diastereomeric salt using D-(−)-tartaric acid and the diastereomers were separated by fractional recrystallization. The pure (1R,3S)-(−)-trans-amine was dimethylated using formic acid/formaldehyde and purified by flash column chromatography to obtain the pure (1R,3S)-(−)-trans-PAT product.

[$^3$H]-Ketanserin (specific activity 72.2 Ci/mmol) and myo-[2-$^3$H(N)]-Inositol (specific activity 18.5 Ci/mmol) were purchased from Perkin-Elmer Life Science (Boston, Mass.) and [N$^6$-methyl-$^3$H]-mesulergine (specific activity 72.0 Ci/mmol) from Amersham Biosciences (GE healthcare, Piscataway, N.J.). Other compounds were obtained in highest purity from Sigma-Aldrich (St. Louis, Mo.).

Clonal Cell Culture and Transfection

All cell lines were maintained by following ATCC suggestion, Chinese Hamster Ovary cells (CHO-K1, ATCC CCL-61) in Ham's F-12 medium supplemented with 10% fetal bovine serum, 1% sodium bicarbonate (Mediatech 25-035-CI), 10 IU/ml Penicillin and 10 ug/ml Streptomycin, and human embryonic kidney (HEK) 293 in minimum essential medium (Eagle) (MEM) with 2 mM L-glutamine adjusted to contain 1.5 g/L sodium bicarbonate, 0.1 mM non-essential amino acids, and 1.0 mM sodium pyruvate (90%) with 10% fetal bovine serum, 10 IU/ml Penicillin and 10 ug/ml Streptomycin. Cells were grown at 37° C. in a humidified incubator with 5% CO2. The cDNAs encoding the human 5-HT$_{2A}$, 5-HT$_{2B}$, and 5-HT$_{2C}$ receptors (wild type) were purchased from UMR (Rolla, Mo.) for transient transfection of the clonal cells. For radioreceptor binding assays, 5-HT$_{2A}$, 5-HT$_{2B}$, and 5-HT$_{2C}$ receptor membranes were prepared from transfected CHO-K1 cells. For functional assays measuring activity of PLC/IP formation, transfected CHO-K1 cells were used for 5-HT$_{2A}$ and 5-HT$_{2C}$ receptors. For 5HT$_{2B}$ receptors, however, more robust and consistent results for the PLC/IP assay were obtained using transfected HEK cells (Setola et al., 2005). Twenty-four hours before transfection, cells were seeded at 40% confluence in 100 mm dishes for radioreceptor binding assays or at $10^5$ cells per well in 12-well plates for functional assays. CHO-K1 cells were transiently transfected with 12 µg of plasmid and 32 µl of lipofectamine (Invitrogen) per 100 mm dish for radioreceptor binding assays, or, 0.8 µg plasmid and 4.0 µl of lipofectamine per well for functional assays. For 5-$HT_{2B}$ functional assays using HEK cells, 24 µg plasmid DNA was mixed with 60 µl of Lipofectamine 2000 (Invitrogen) to transfect 1-2×$10^6$ cells in a 10-cm plate. Cells were allowed to express transfected receptors for another 24 hrs (Herrick, 1997).

Radioreceptor Assays

Radioreceptor saturation and competition binding assays were performed using membrane homogenates, similar to our methods reported previously for the phylogenetically closely related histamine $H_1$ GPCR (Booth, 2002; Moniri et al., 2004). [$^3$H]-Ketanserin was used to radiolabel 5-$HT_{2A}$ receptors and [$^3$H]-mesulergine for 5-$HT_{2B}$ and 5-$HT_{2C}$ receptors. Briefly, forty-eight hours following CHO cell transfection, cells were harvested and homogenized in 50 mM Tris-HCl containing 0.1% ascorbic acid and 4.0 mM $CaCl_2$ at pH 7.4 (assay buffer). The homogenate was centrifuged at 35,000 g for 25 min and the resulting membrane pellet was re-suspended in assay buffer. Protein concentration was determined by the method of Lowry et al. (Lowry, 1951). For saturation binding assays, membrane suspension containing 100 µg protein was incubated with 0.1-5.0 nM [$^3$H]-ketanserin (5-$HT_{2A}$ receptors) or 0.1-20 nM [$^3$H]-mesulergine (5-$HT_{2B}$ and 5-$HT_{2C}$ receptors) in a total assay buffer volume of 250 µl. Non-specific binding was determined in the presence of 10 µM methysergide (5-$HT_{2A}$ receptors) or 1.0 µM mianserin (5-$HT_{2B}$ and 5-$HT_{2C}$ receptors). Competition binding assays were conducted similarly with 1.0 nM [$^3$H]-ketanserin or [$^3$H]-mesulergine. Incubation of radioreceptor binding assay mixtures was for 1.0 h at 37° C., with termination by rapid filtration through Whatman GF/B filters using a 96-well cell harvester (Tomtec, Hamden, Conn.). The membrane-bound [$^3$H]-radioligand retained on the filter discs was quantified by liquid scintillation spectrometry. Data were analyzed by non-linear regression using the sigmoidal curve-fitting algorithms in Prism 4.03 (GraphPad Software Inc., San Diego, Calif.). Ligand affinity is expressed as an approximation of $K_i$ values by conversion of the $IC_{50}$ data to $K_{0.5}$ values using the equation $K_{0.5}=IC_{50}/1+L/K_D$, where L is the concentration of radioligand having affinity $K_D$ (Cheng, 1973). Each experimental condition was performed in triplicate and each experiment was performed a minimum of three times to determine S.E.M.

Assay for Activation of PLC and [$^3$H]-IP Formation

Functional activation of PLC was measured as [$^3$H]-IP formation in CHO cells transiently expressing serotonin 5-$HT_{2C}$ receptors or HEK cells transiently expressing serotonin 5-$HT_{2A}$ or 5-$HT_{2B}$ receptors, as previously reported (Moniri et al., 2004). Briefly, thirty-two hours following transfection, cells in inositol-free Dulbecco's modified Eagle's medium (DMEM) were incubated for twelve hours with 1.0 µCi/ml myo-[2-$^3$H]-inositol, the radiolabeled precursor of the PLC-β substrate phosphatidylinositol. Cells then were washed and incubated in DMEM containing 10 mM lithium chloride, 10 µM pargyline (with addition of 5% dialyzed fetal bovine serum for HEK cells), and, various concentrations of test ligand for 45-60 min at 37° C. After aspiration of media, wells were lysed by incubation with 50 mM formic acid (15-60 min). Formic acid was neutralized with ammonium hydroxide and contents from each well were added to individual AG1-X8 200-400 formate resin anion exchange columns. Ammonium formate/formic acid (1.2 M/0.1 M) was used to elute [$^3$H]-IP directly into scintillation vials for counting of tritium by liquid scintillation spectrometry. Resulting data were analyzed using the nonlinear regression algorithms in Prism 4.03 and are expressed as mean percentage of control [$^3$H]-IP formation, with potency expressed as concentration required to stimulate ($EC_{50}$) or inhibit ($IC_{50}$) maximal basal (constitutive) [$^3$H]-IP formation by 50%±S.E.M. (n≥3).

Measurement of [$^3$H]-IP Formation in CHO-K1 and HEK Cells

Functional activation of PLC was measured as [$^3$H]-IP formation in CHO cells transiently expressing 5-$HT_{2A}$ or 5-$HT_{2C}$ receptors and HEK cells transiently expressing 5$HT_{2B}$ receptors, as previously reported by our lab (Booth, 2002; Moniri et al., 2004). Briefly, thirty-two hours following transfection, cells in inositol-free Dulbecco's modified Eagle's medium (DMEM) were labeled with 1 µCi/ml myo-[2-$^3$H]-inositol, a precursor of the PLC-β substrate phosphatidylinositol. Cells then were washed and incubated in DMEM containing 25 mM Hepes (pH 7.4), 10 mM LiCl, 10 µM pargyline (with addition of 5% dialyzed FBS for HEK cells), and various concentrations of test ligand for 45-60 min at 37° C. After aspiration of media, wells were placed on ice and lysed by incubation with 50 mM formic acid (15-60 min). Formic acid was neutralized with ammonium hydroxide and all contents from each well were added to individual AG1-X8 200-400 formate resin anion exchange columns. Ammonium formate/formic acid (1.2 M/0.1 M) was used to elute [$^3$H]-IP directly into scintillation vials for counting of tritium by liquid scintillation spectrometry. Resulting data were analyzed using the nonlinear regression algorithms in Prism 4.03 and are expressed as mean percentage of control [$^3$H]-IP formation, with potency expressed as concentration required to produce 50% maximal [$^3$H]-IP formation ($EC_{50}$)±S.E.M (n≥3).

Example 4

Radioreceptor Assays

Figure 2A:
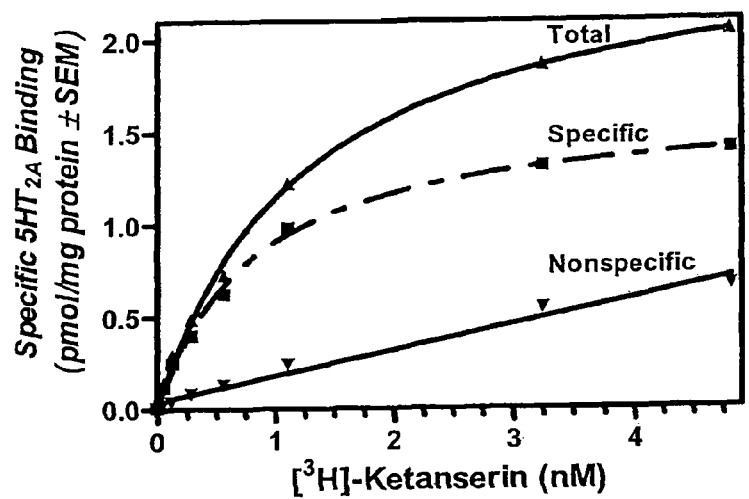
FIG. 2. depicts (2A-2C) representative binding curves for [$^3$H]-ketanserin labeled 5HT$_{2A}$ receptors and [$^3$H]-mesulergine labeled 5-HT$_{2B}$ receptors and 5-HT$_{2C}$ receptors.
Figure 2B:
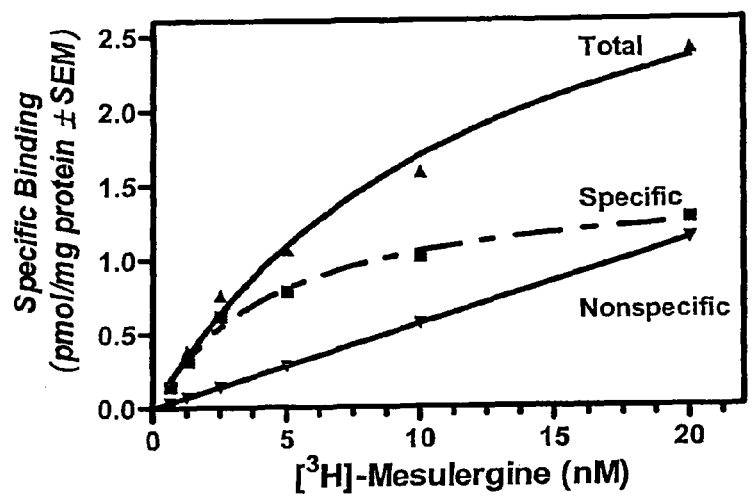
Figure 2C:
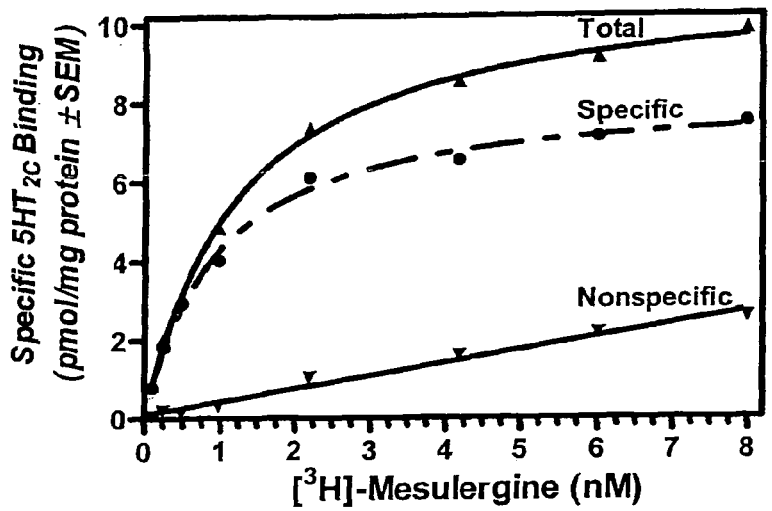

Radioligand Saturation Binding Analysis of 5HT-Subtype Receptors:

There was no measurable specific radioligand binding using membranes prepared from null-transfected CHO and HEK cells. Using membranes prepared from CHO cells transiently transfected with 5-$HT_{2A}$, 5-$HT_{2B}$, or 5-$HT_{2C}$ cDNA, however, saturable specific radioligand binding occurs—representative binding curves for [$^3$H]-ketanserin labeled 5$HT_{2A}$ receptors and [$^3$H]-mesulergine labeled 5-$HT_{2B}$ receptors and 5-$HT_{2C}$ receptors are shown in FIGS. 2A-C. [$^3$H]-Ketanserin binds to an apparent single population of 5$HT_{2A}$ receptors ($B_{max}$=1.73±0.11 pmol/mg protein) with high affinity ($K_D$=0.80±0.03 nM). Similarly, [$^3$H]-mesulergine labels a single population of 5$HT_{2B}$ receptors with $B_{max}$=1.13±0.39 pmol/mg protein and $K_D$=5.19±0.36 nM. [$^3$H]-mesulergine also labels an apparent single population of 5$HT_{2C}$ receptors ($B_{max}$=8.37±0.15 pmol/mg prot) with high affinity ($K_D$=0.88±0.03 nM).

Example 5

Figure 3:
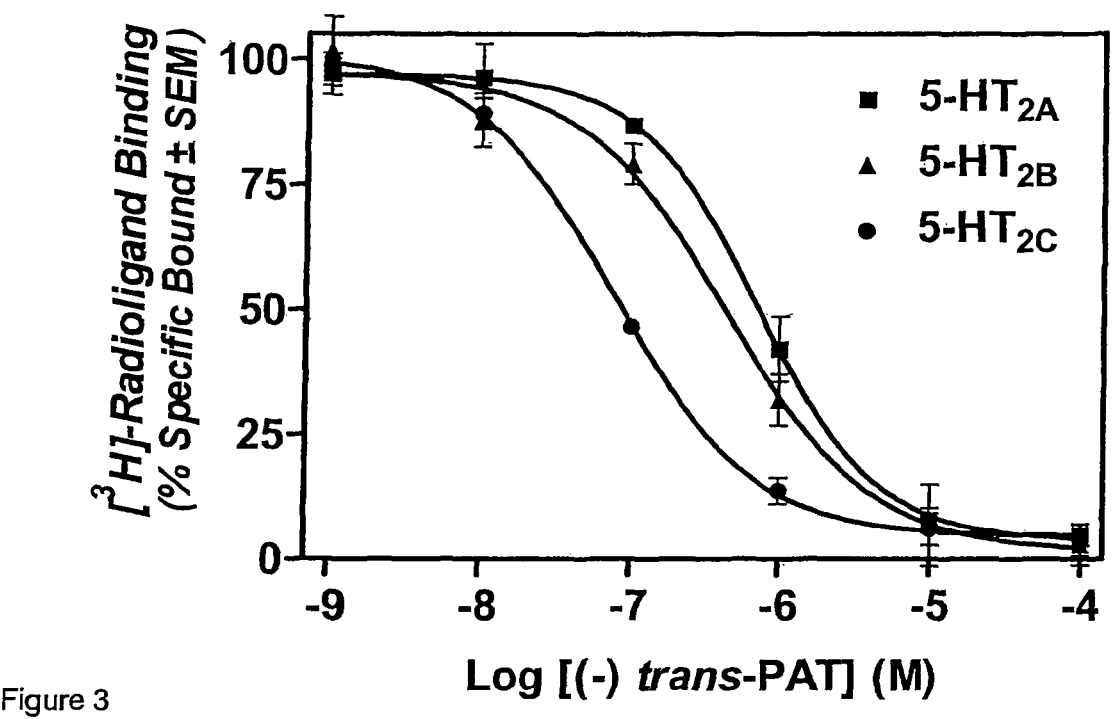
FIG. 3. depicts representative 5-HT$_{2A}$, 5-HT$_{2B}$, and 5-HT$_{2C}$ radioligand displacement curves for (−)-trans-PAT.

Competition Binding Analysis to Determine (−)-Trans-PAT 5$HT_2$-Subtype Receptor Affinity Representative 5-$HT_{2A}$, 5-$HT_{2B}$, and 5-$HT_{2C}$ radioligand displacement curves for (−)-trans-PAT are shown in FIG. 3.

Curves are sigmoidal in shape and span 3-4 log ligand concentration units to achieve complete radioligand displacement, characteristic of competitive displacement of ~$K_D$ radioligand concentration from a single population of GPCRs. The $K_i$±SEM values for (−)-trans-PAT at $5HT_{2A}$, $5-HT_{2B}$, and $5-HT_{2C}$ receptors are 410±38, 130±28, and 37.6±3.02 nM (respectively), with corresponding $n_H$ values of 1.1±0.1, 1.1±0.1, and 0.9±0.1.

Example 6

Functional Assays

Figure 4:
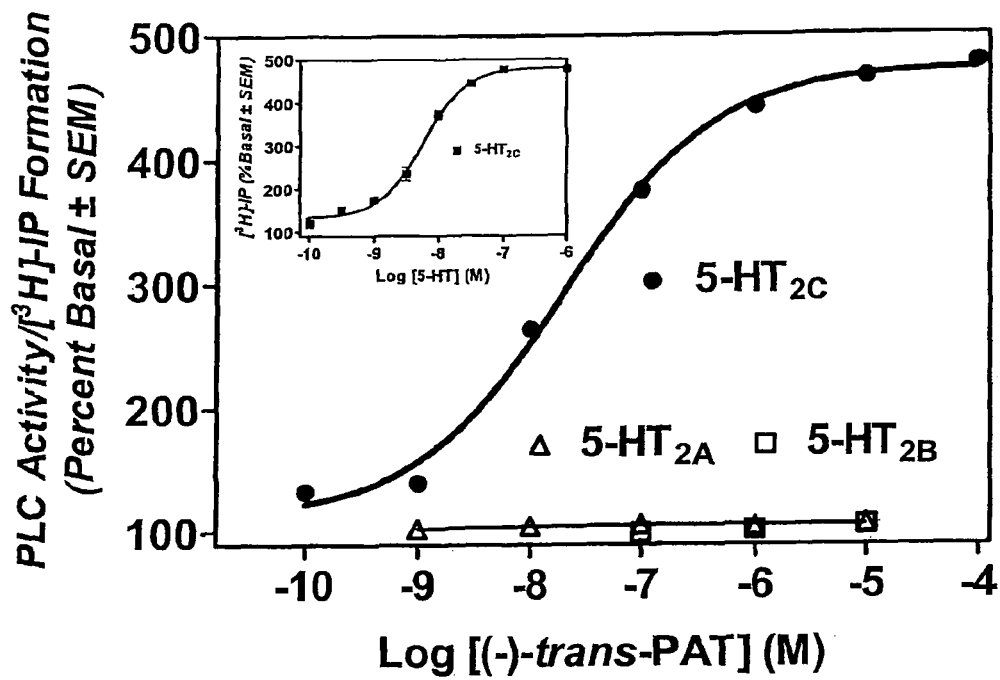
FIG. 4. depicts assessment of (−)-trans-PAT agonist activity at 5HT$_2$-subtype receptors.

Assessment of (−)-Trans-PAT Agonist Activity at $5HT_2$-Subtype Receptors:

The $5HT_2$ GPCR family is constitutively active when expressed in CHO and HEK cells, thus, functional activity here is reported relative to basal activity of PLC/[$^3$H]-IP formation in FIG. 4. In lysates of null-transfected CHO and HEK cells, no increase in basal activity of PLC/[$^3$H]-IP formation was detected after incubation with up to 10 μM 5-HT for 45 min. In CHO cells transiently transfected with human $5-HT_{2C}$ cDNA, however, 5-HT produces a concentration-dependent increase in basal activity of PLC/[$^3$H]-IP formation, with $EC_{50}$=6.30±0.55 nM ($n_H$=1.3±0.2) and $E_{max}$~0.1 μM (~475% basal control activity), as shown in the FIG. 4 inset. Relative to the endogenous agonist, (−)-trans-PAT is a full-efficacy $5HT_{2C}$ agonist that produces a concentration-dependent increase in basal activity of PLC/[$^3$H]-IP formation, with $EC_{50}$=21.4±2.22 nM ($n_H$=0.66±0.11) and $E_{max}$~10 μM (~475% basal control activity) (FIG. 4). In CHO cells transiently transfected with human $5HT_{2A}$ cDNA, however, (−)-trans-PAT did not stimulate PLC/[$^3$H]-IP formation at concentrations up to 10 μM; for comparison, 5HT $EC_{50}$=30±2 nM, $E_{max}$~1.0 μM (~300% basal control activity) (data not shown). Likewise, in HEK cells transiently transfected with human $5HT_{2B}$ cDNA, (−)-trans-PAT did not stimulate PLC/[$^3$H]-IP formation at concentrations up to 30 μM; for comparison, 5HT $EC_{50}$=19.7±9.21 nM, $E_{max}$~1.0 μM (~900% basal control activity (data not shown).

Example 7

Assessment of (−)-Trans-PAT Antagonist Activity at $5HT_2$-Subtype Receptors

Figure 5A:
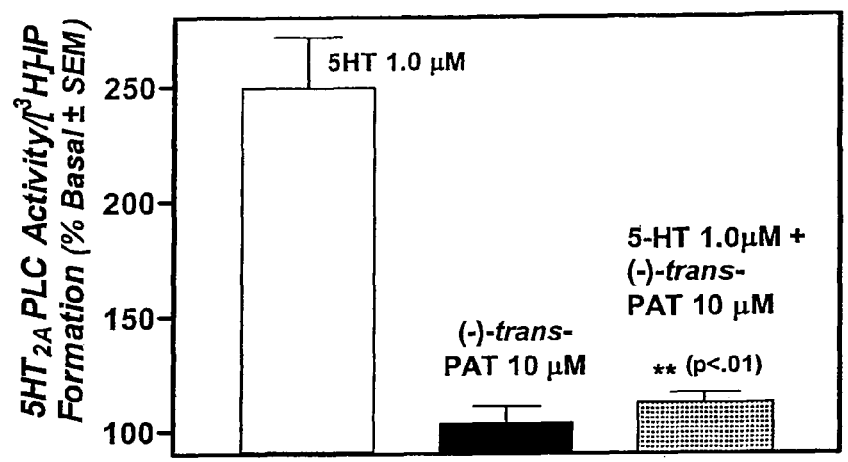
FIG. 5. depicts assessment of the ability of (−)-trans-PAT to act as a 5HT$_{2A}$ and 5HT$_{2B}$ receptor antagonist regarding 5-HT-mediated stimulation of PLC/[$^3$H]-IP formation.
Figure 5B:
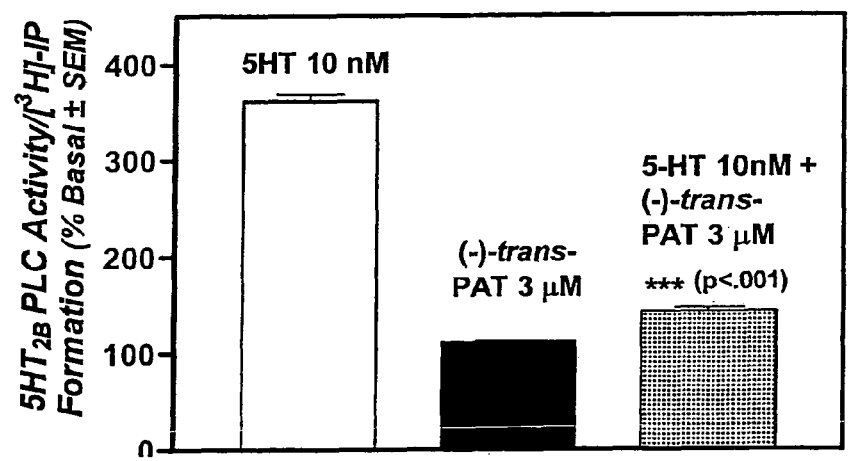

Given that (−)-trans-PAT binds with moderate affinity to $5HT_{2A}$ and $5HT_{2B}$ receptors (FIG. 3) but does not activate these 5-HT2 receptor subtypes (FIG. 4), the ability of (−)-trans-PAT to act as a $5HT_{2A}$ and $5HT_{2B}$ receptor antagonist regarding 5-HT-mediated stimulation of PLC/[$^3$H]-IP formation was assessed and results are shown in FIG. 5. In CHO cells expressing human $5HT_{2A}$ receptors, 5-HT (1.0 μM) stimulated PLC/[$^3$H]-IP formation (~250% basal control) and this effect was fully blocked by (−)-trans-PAT (10 μM) (FIG. 5A). In HEK cells expressing human $5HT_{2B}$ receptors, 5-HT (0.01 μM) stimulated PLC/[$^3$H]-IP formation (~350% basal control) and this effect was fully blocked by (−)-trans-PAT (3.0 μM) (FIG. 5B).

Example 8

Discussion

The data reported here indicate that relative to the endogenous agonist serotonin, (−)-trans-PAT is a stereoselective full-efficacy agonist at human serotonin $5-HT_{2C}$ receptors. The selectivity of (−)-trans-PAT for activation of $5-HT_{2C}$ receptors versus $5-HT_{2A}$ and $5-HT_{2B}$ receptors is unequivocal in light of its competitive antagonism of serotonin activation of $5-HT_{2A}$ and $5-HT_{2B}$ receptors, and, its inherent inverse agonist functional activity at $5-HT_{2A}$ and $5-HT_{2B}$ receptors. The unique multifunctional activity of (−)-trans-PAT at serotonin $5-HT_2$-type receptors is promising with regard to development of novel $5-HT_{2C}$ receptor-based pharmacotherapy. Results indicate that (−)-trans-PAT demonstrates full-efficacy for activation of human $5HT_{2C}$ receptors as well as inverse agonist and/or antagonist activity at $5HT_{2A}$ and $5HT_{2B}$ receptors. These results have promising implications for development of novel $5HT_{2C}$-based pharmacotherapy. For example, activation of brain $5HT_{2C}$ receptors is well established to be effective pharmacotherapy for obesity (Tecott et al., 1995; Vickers et al., 1999; 2001; Heisler et al., 2002). Meanwhile, there currently is no effective pharmacotherapy for cocaine addiction. It is thought, however, that disorders involving over-eating and drug self-administration are members of the same group of compulsive behavioral disorders directed toward different objects, food and drugs (Simansky, 2005). Accordingly, a role for brain $5HT_{2C}$ receptor activation in pharmacotherapy of both obesity and cocaine addiction appears logical. In fact, the balance of studies using reliable $5HT_2$ subtype-selective antagonists suggest that the reinforcing effects of cocaine are reduced by $5HT_{2C}$ activation, and, discriminative stimulus and reinstating effects of cocaine are sensitive to attenuation by $5HT_{2C}$ activation as well as by $5HT_{2A}$ antagonism (Bubar and Cunningham, 2006).

Figure 17:
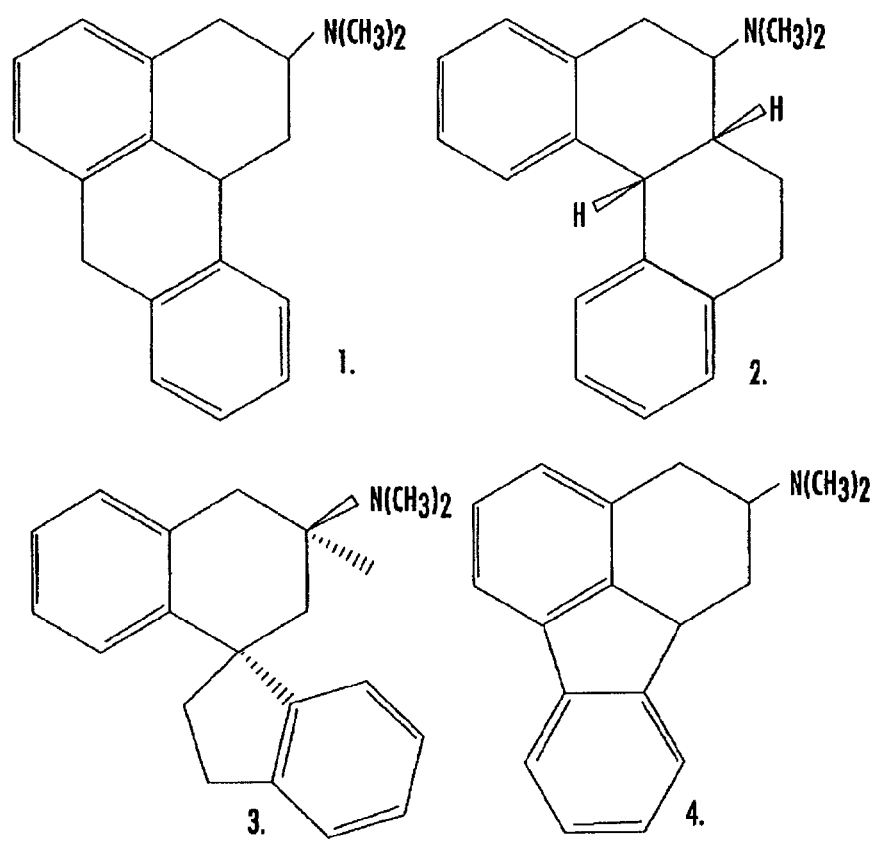
FIG. 17. (Example 11, 2 FIG. 16) depicts PATS having fixed pendant phenyl rings.
Figure 18:
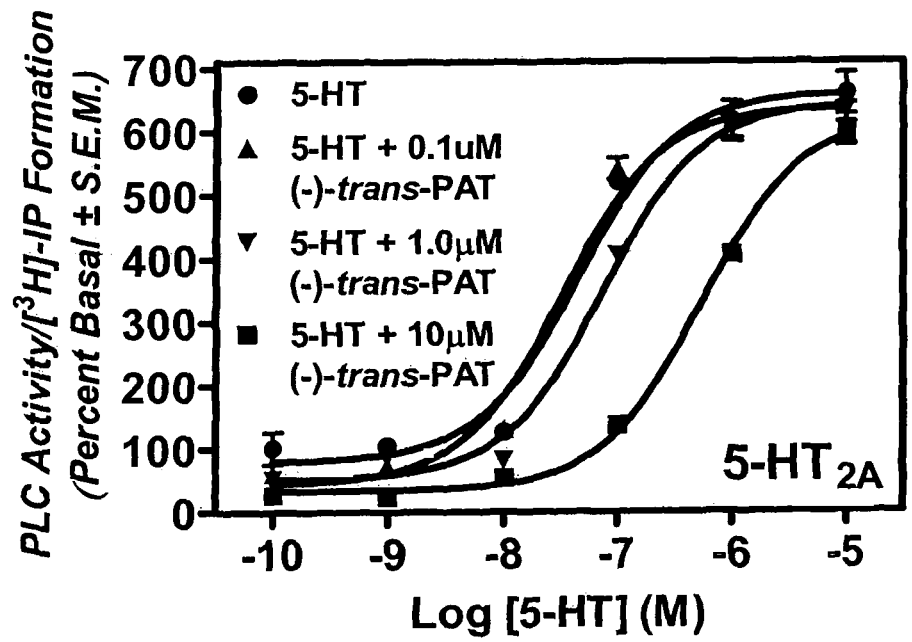
FIG. 18. depicts (−)-Trans-PAT competitive antagonism of 5-HT activation of 5-HT$_{2A}$ receptors.
Figure 19:
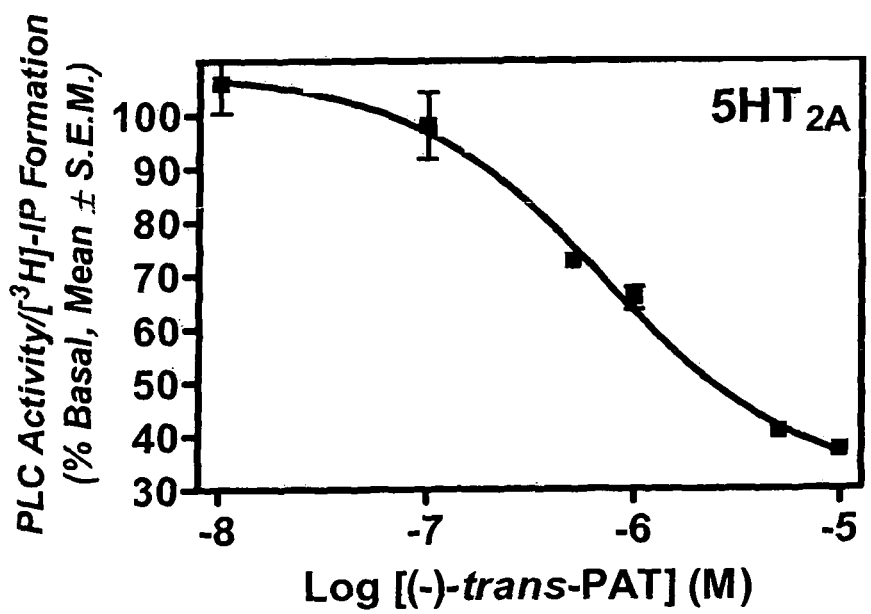
FIG. 19. depicts (−)-Trans-PAT inverse agonist activity at serotonin 5-HT2$_A$ receptors.

In contrast, $5HT_{2A}$ receptor activation is closely associated with psychomimetic activity (Nichols, 2004), as perhaps best demonstrated by the inverse observation that drugs with $5HT_{2A}$ antagonist activity are effective to treat psychosis and related neuropsychiatric disorders (Baldessarini and Tarazi, 2006). Thus, the possibility of $5HT_{2A}$ receptor activation concomitant with $5HT_{2C}$ activation for drugs that show only modest 15-fold selectivity in vitro, such as lorcaserin (Jensen, 2006; Smith et al., 2006), should be carefully considered in view of the sometimes subtle and complex nature of psychiatric disturbances. Perhaps, the life-threatening cardiac valvulopathy and pulmonary hypertension associated with fenfluramine has led to a higher threshold for selectivity (e.g., 100-fold, in vitro) regarding development of drugs that activate both $5HT_{2C}$ and $5HT_{2B}$ receptors. Nevertheless, clinical use of a diet drug by perhaps 30-50 million people (Nilsson, 2006; Smith et al., 2006), often chronically, often unsupervised, could lead to problems if the drug demonstrates any activation of $5HT_{2A}$ and/or $5HT_{2B}$ receptors. We have made an extra effort to ensure that any lead compounds we put forward for drug development demonstrate unequivocal $5HT_{2B}$ antagonism by switching to HEK cells because this clonal cell line gives more robust and reproducible functional results compared to CHO cells for the $5HT_{2B}$ receptor. Thus, a $5HT_{2C}$ agonist such as (−)-trans-PAT, that demonstrates unequivocal $5HT_{2A}$ and $5HT_{2B}$ inverse agonism and/or antagonism, and is a small lipophilic molecule that penetrates mammalian brain after peripheral administration, appears to be well-suited for consideration as novel pharmacotherapy for obesity, cocaine addiction, psychosis, anxiety, and, perhaps other neuropsychiatric disorders. In this regard, the unequivocal $5-HT_{2A}$ inverse agonist/antagonist activity demonstrated by (−)-trans-PAT (see, FIGS. 17, 18) suggests psychiatric side-effects linked to $5-HT_{2A}$ receptor activation likely would not be an issue for this compound.

Example 9

1b. Activity of PAT Analogs at GPCRs

Affinity of PAT analogs in Tables 1 for the histamine $H_1$ GPCR is known and Ki range is 0.5-5,000 nM (Ghoneim et al., 2006; Booth et al., 2002; Bucholtz et al., 1999; each incorporated by reference therein). As mentioned, there is virtually no molecular information published about ligand-$5HT_{2C}$ receptor binding site interactions, but, our preliminary data indicate there are differences in comparison to the $H_1$ receptor. There is information about the $H_1$ binding site from computational chemistry (QSAR) and receptor modeling studies (e.g., Ghoneim et al., 2006; Jongejan and Leurs, 2005; Jongejan et al., 2005) that facilitates prediction of ligand $H_1$ affinity. The relative lack of corresponding studies for the $5HT_{2C}$ receptor, however, does not allow for prediction of which $H_1$-active ligands will have affinity at $5HT_{2C}$ receptors.

A number of the PAT analogs have been evaluated for $H_1$ functional activity. In view of the apparently subtle and largely unknown molecular determinants that govern ligand activation of a GPCR, it is perhaps not surprising that most of the PATs are $H_1$ antagonists, but 1 and 6 activate $H_1$-linked AC and PLC signaling, respectively (Moniri et al., 2004; Moniri and Booth, 2006). For both $H_1$ binding and function, stereochemistry significantly influences activity.

In addition to our $H_1$ and $5HT_2$ results reported herein, several analogs in Table 1 were evaluated for affinity at a wide variety of CNS receptors (PDSP, 2005; Novascreen, 1996). Our lead $5HT_{2C}$ agonist molecule, (−)-trans-PAT (1), has very low ($K_i$>0.5 μM) or virtually no ($K_i$>5 μM) affinity for ~35 radiolabeled CNS receptor systems, including, neurotransmitter (adrenergic $α_{2A}$, $α_1$, $β_1$, $β_2$; cholinergic; GABA; glycine; histamine $H_2$, $H_3$, H4; serotonin $5HT_{1A}$, $5HT_{1B}$), neuromodulator (adenosine, benzodiazepine, opiate, NMDA/PCP, sigma), neurotransporter (DAT, NET, SERT), ion channel ($Ca^{++}$, $Cl^-$, $K^+$), and second messenger systems (AC, PLC). The affinity (Ki) of racemic (±)-trans-PAT for $5HT_{5A}$, $5HT_6$, and $5HT_7$ receptors is about 100, 200, and 0.5 nM, respectively, and, affinity at adrenergic $α_{2B}$ and $α_{2C}$ receptors is 150 and 300 nM, respectively (PDSP, 2005).

1c. Radioligand Saturation Binding Experiments for Human $5HT_{2A}$, $5HT_{2B}$, and $5HT_{2C}$ Receptors Transiently Expressed in CHO Cells (FIGS. 2-4)

Radioreceptor assays were set up in our lab for $5HT_{2A}$, $5HT_{2b}$, and $5HT_{2C}$ receptors and saturation binding analysis was performed to determine, in our hands, respective radioligand $K_D$ and $B_{max}$. Twenty-four hours before transfection, CHO-K cells were seeded at 40% confluence in 100 mm dishes for binding assays (or at $10^5$ cells per well in 12-well plates for [$^3$H]-IP assay, below). The cDNAs encoding the human 5-$HT_{2A}$, 5-$HT_{2B}$, or 5-$HT_{2C}$ receptor (wild type) were purchased from UMR resource center (Rolla, Mo.). Cells were transfected with 12 μg of plasmid and 32 μl lipofectamine (Invitrogen) per 100 mm dish or 0.8 μg of plasmid and 4.0 μl of lipofectamine (Invitrogen) per well according to manufacturer protocols, our previous experience (Ghoneim et al, 2006; Moniri et al, 2004; Booth et al., 2002) and the literature (Herrick-Davis et al, 1997). Receptors were radiolabeled with standard $5HT_2$ antagonist radioligands, using [$^3$H]-ketanserin for $5HT_{2A}$ receptors and [$^3$H]-mesulergine for $5HT_{2B}$, and $5HT_{2C}$ receptors (Knight et al., 2004). Representative curves are in FIGS. 2-4 and $K_D$ and $B_{max}$ summary in Table 3; values are consistent with literature (Knight et al., 2004).

TABLE 3

|  | $K_D$ ± SEM (nM) | $B_{max}$ ± SEM (pmol/mg prot) |
|---|---|---|
| $5HT_{2A}$ | 0.80 ± 0.03 | 1.73 ± 0.11 |
| $5HT_{2B}$ | 5.20 ± 0.61 | 1.13 ± 0.67 |
| $5HT_{2C}$ | 0.88 ± 0.03 | 8.37 ± 0.15 |

In view of unknown functional activity for most of our novel ligands, agonist radioligands were not used here because they label only a subpopulation of receptors in the "agonist-preferring" conformation (Knight et al., 2004; Sleight et al. 1996; Roth et al. 1998; Lopez-Gimenez et al. 2001; Quirk et al. 2001). Agonist-preferring conformation(s) for the $5HT_2$ GPCR family is accounted for within the framework of the three-state model of GPCR activation, wherein GPCRs isomerize between inactive and constitutively active states (Kenakin, 2001). A critical assumption of revised GPCR signaling theory is that a heterogeneity of active receptor conformations exists and that agonist ligands differ in their ability to induce, stabilize, or select among receptor conformations. It follows that agonist ligand chemical structural parameters are among the most important determinants of GPCR conformation (Moniri et al., 2004). Currently there are no selective $5HT_{2C}$ agonist radioligands available, thus, selective PAT $5HT_{2C}$ agonists with an N-alkyl moiety and Ki<5 nM will be considered for radiolabeling via our published procedures (Wyrick et al., 1992; 1994)

1d. Competition Binding Experiments

Affinity of Trans-(−)-PAT Stereoisomers at $5HT_{2c}$ Receptors (FIG. 5, Table 4)

The $5HT_{2C}$ receptor affinity of (−)-trans-PAT and its stereoisomers, (+)-trans-PAT, (−)-cis-PAT, and (+)-cis-PAT, was assessed in competitive radioligand displacement assays using ~$K_D$ concentration of radioligand (as determined above). Curves (FIG. 5) are sigmoidal and span 3-4 log concentration units to achieve complete radioligand displacement, characteristic of competitive displacement of ~$K_D$ radioligand concentration. The Hill coefficient ($n_H$) for the slope of the competitive displacement curve for (−)-trans-PAT is 0.9, characteristic of agonist ligand binding at a GPCR, according to the ternary complex model with limiting availability of G protein, and, subpopulation(s) of receptor in an agonist-preferring conformation(s). The $n_H$ values for the other PAT stereoisomers range 0.8-1.0 (antagonists theoretically should have $n_H$=1). Except for (−)-trans-PAT, none of the other PAT stereoisomers activate $5HT_{2C}$ receptors at concentrations up to 10 μM (i.e., at least 10-times Ki)—see Aim 2 results. The stereoselectivity of $5HT_{2C}$ receptors for PAT isomers has significant applications to delineate the 3D structure of the $5HT_{2C}$ active site and molecular determinants for receptor activation.

TABLE 4

| PAT Stereoisomer | $5HT_{2C}$ Ki ± SEM | $n_H$ |
|---|---|---|
| (1R,3S)-(−)-trans-PAT | 37.6 ± 3.0 nM | 0.9 |
| (+/−)-trans-PAT (not shown in FIG. 5 for clarity) | 75.0 nM ± 2.2 nM | 0.7 |
| (1S,3R)-(+)-trans-PAT | 1270 ± 84.8 nM | 1.0 |
| (1S,3S)-(−)-cis-PAT | 433 ± 4.8 nM | 0.8 |
| (1R,3R)-(+)-cis-PAT | 975 ± 7.8 nM | 0.8 |

1e. Affinity of Trans-(−)-PAT Stereoisomers at 5HT$_{2A}$ Receptors (FIG. 6)

Figure 6:
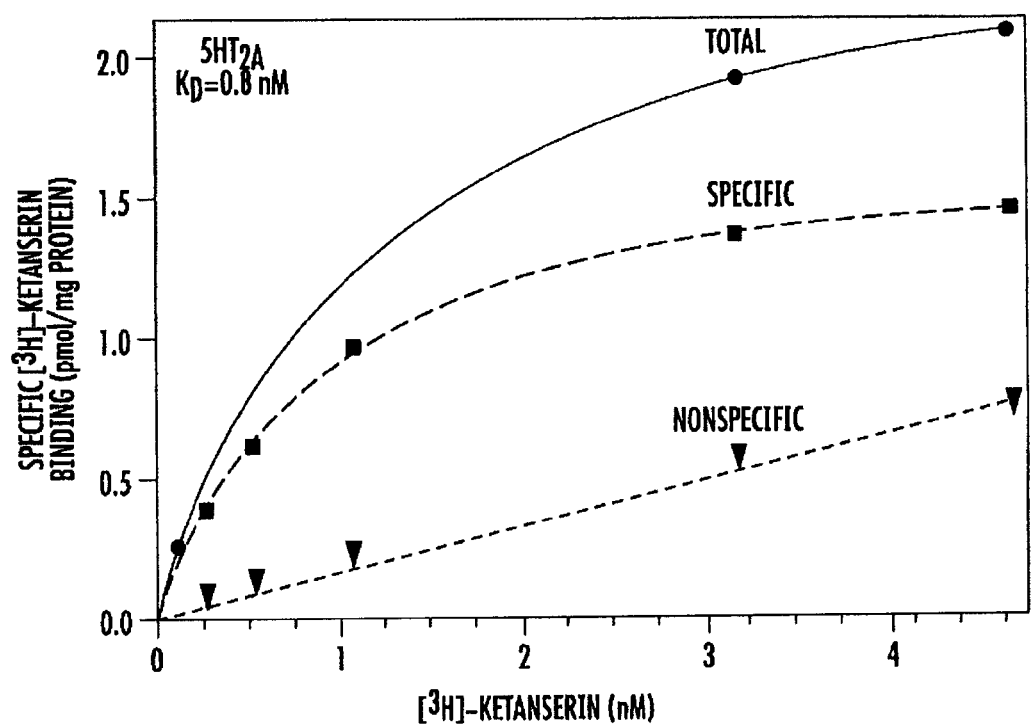
FIG. 6. (Example 9, 1(c) FIG. 2) depicts curves for 5-HT$_{2A}$ binding
Figure 10:
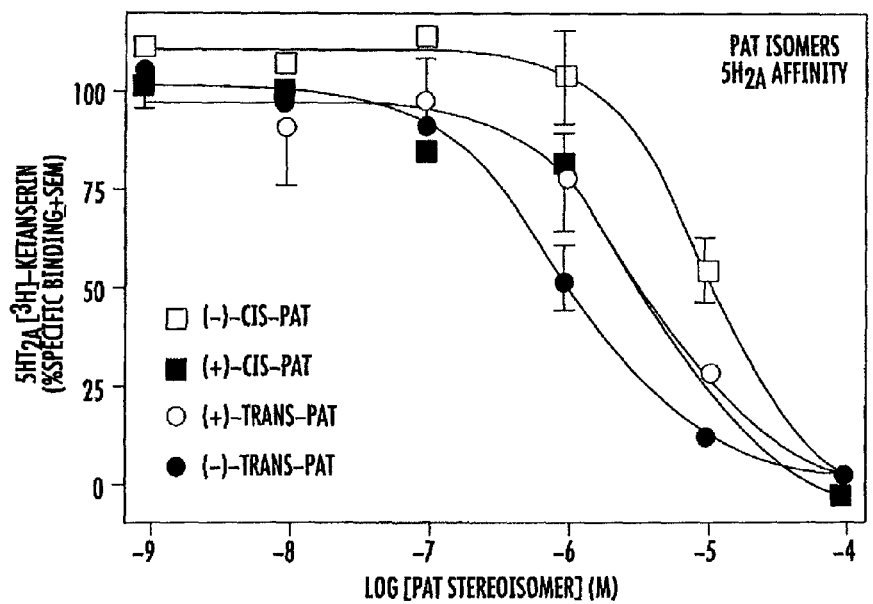
FIG. 10. (Example 9, 1(d) FIG. 6) depicts curves for 5-HT$_{2A}$ binding.
Figure 11:
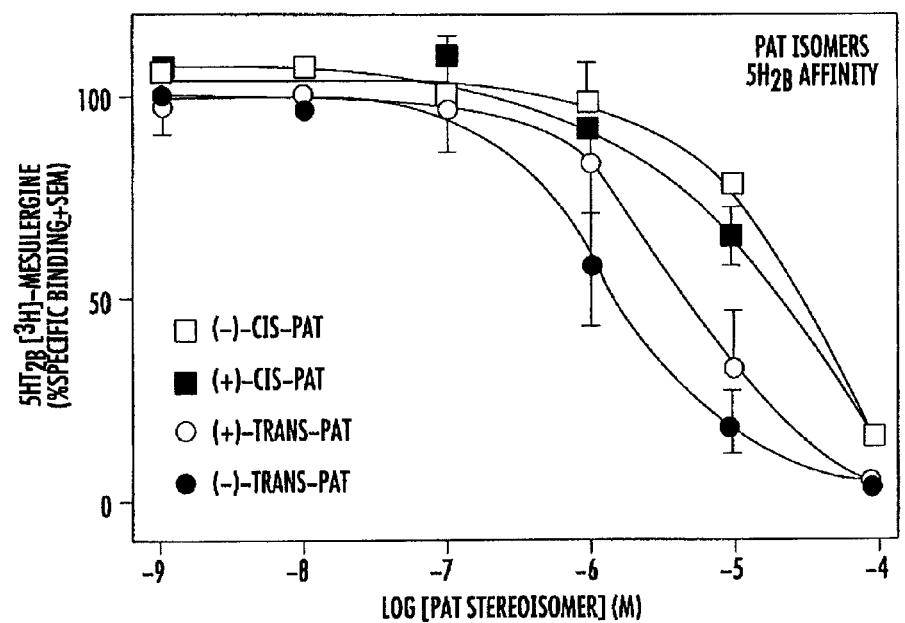
FIG. 11. (Example 9, 1(d) FIG. 7) depicts curves for 5-HT$_{2C}$ binding.

Concentration-response curves for radioligand displacement by (−)-trans-PAT and its stereoisomers at 5HT$_{2A}$ receptors is shown in FIG. 6. The 5HT$_{2A}$ affinity of (−)-trans-PAT (Ki~400 nM) is 10-fold lower than at 5HT$_{2C}$ receptors. Table 5 summarized Ki and n$_H$ values for all 4 PAT stereoisomers. The rank order for affinity of PAT stereoisomers at 5HT$_{2A}$ receptors is different than at 5HT$_{2C}$ receptors; rank order at 5HT$_{2A}$ also differs from histamine H$_1$ receptors. The n$_H$ value for (−)-trans-PAT at 5HT$_{2A}$ is 0.9, however, it is a 5HT$_{2A}$ antagonist (FIGS. 10,11). The functional assay is not sensitive enough to detect inverse agonism, but, such activity is likely. Functional assessment of other PAT stereoisomers at 5HT$_{2A}$ (n$_H$=0.9-1.0) is not complete.

1f. Affinity of Trans-(−)-PAT Stereoisomers at 5HT$_{2B}$ Receptors (FIG. 7)

Figure 7:
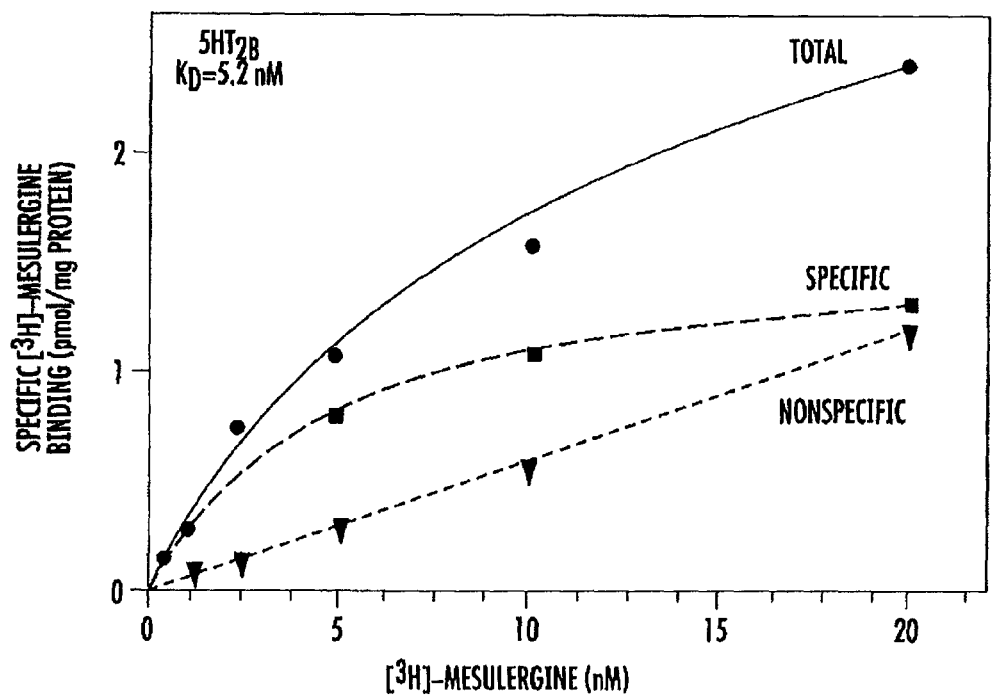
FIG. 7. (Example 9, 1(c) FIG. 3) depicts curves for 5-HT$_{2B}$ binding.
Figure 12:
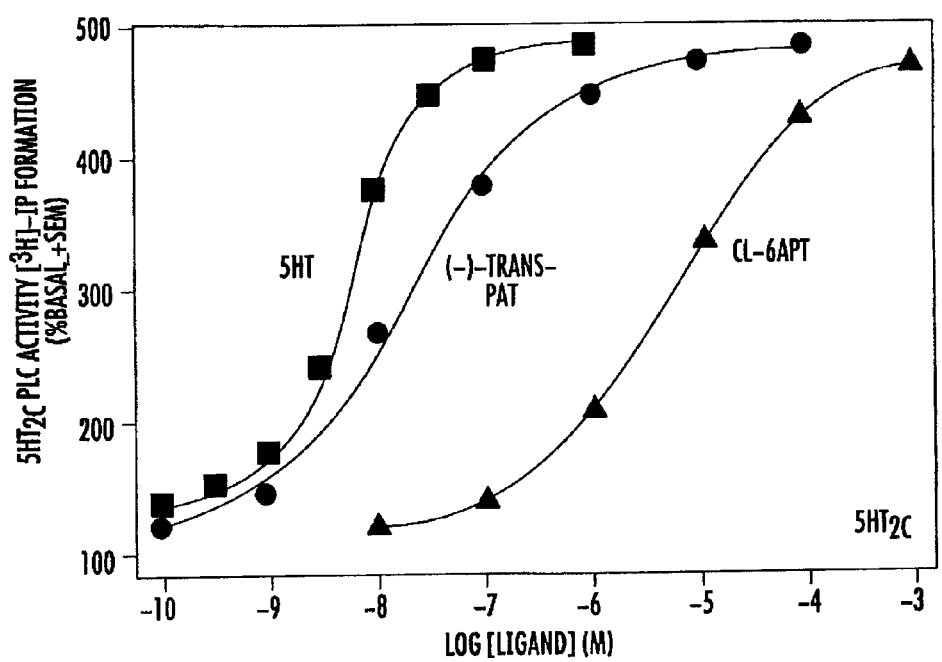
FIG. 12. (Example 10, 2(a) FIG. 9) depicts curves for phospholipase C (PLC) activity.

Concentration-response curves for radio-ligand displacement by (−)-trans-PAT and its stereoisomers at 5HT$_{2B}$ receptors is shown in FIG. 7. The 5HT$_{2B}$ affinity of (−)-trans-PAT (Ki~1 μM) is 20-fold lower than at 5HT$_{2C}$ receptors. The n$_H$ value for (−)-trans-PAT at 5HT$_{2A}$ is 1.0, consistent with its 5HT$_{2B}$ antagonist activity (FIGS. 10,12). Ki and n$_H$ values for all 4 PAT stereoisomers are summarized in Table 5. Rank order of PAT stereoisomer binding at 5HT$_{2B}$ receptors is different and overall much lower than at 5HT$_{2A}$ and 5HT$_{2C}$ receptors. Thus, although amino acid sequence is very similar for members of the 5HT$_2$ family, the 3D arrangement of amino acids that form the PAT ligand binding site appears to be different (especially for the 5HT$_{2B}$ receptor). Thus the PAT stereochemical scaffold can be used as a template for molecular modeling (structural) studies and optimized to provide drugs with selective actions at 5HT$_2$ subtypes.

(Shapiro et al., 2000)—this information helps to guide future 5HT$_{2C}$ mutagenesis and molecular modeling studies.

(+)-Trans-, (−)-cis-, and (+)-cis-PAT also were evaluated for ability to activate 5HT$_{2C}$ receptors (PLC/[$^3$H]-IP formation). FIG. 10 shows that at 1.0 μM and 10 μM (i.e., at least 10-times Ki), (+)-trans-, (−)-cis-, and (+)-cis-PAT are not 5HT$_{2C}$ agonists. Thus, the (−)-trans-PAT functional effect is stereo-specific, consistent with the >30-fold range in binding affinity between the stereoisomers at 5HT$_{2C}$ receptors.

Interestingly, the potency of (−)-trans-PAT to activate 5HT$_{2C}$ receptors (EC$_{50}$~20 nM) is about 2-fold higher than its 5HT$_{2C}$ affinity when measured using an antagonist radioligand (Ki~40 nM, FIG. 5). In this regard it is noted that antagonist radioligands do not distinguish the "agonist-preferring" conformation of the receptor (Roth et al. 1998; Lopez-Gimenez et al. 2001; Quirk et al. 2001). In fact, the Ki of (−)-trans-PAT for the agonist-preferring conformation of the 5HT$_{2C}$ receptor may be closer to 20 nM rather than 40 nM. Studies will be conducted using the standard (but nonselective) 5HT$_2$ agonist radioligand, [$^3$H]-2,5-dimethoxy-4-iodoamphetamine to confirm this.

2b. (−)-Trans-PAT does not Activate 5HT$_{2A}$ or 5HT$_{2B}$ Receptors (FIG. 11).

As shown in FIG. 11, in CHO cells expressing human 5HT$_{2A}$ or 5HT$_{2B}$ receptors, (−)-trans-PAT did not activate PLC/IP formation, even at 10 μM (~25-times and 70-times 5HT$_{2A}$ and 5HT$_{2B}$ receptor Ki value, respectively). In parallel assays using CHO-5HT$_{2C}$ cells, results were similar to those above. To the best of our knowledge, there is no other ligand reported that activates 5HT$_{2C}$ receptors that does not also activate 5HT$_{2A}$ and/or 5HT$_{2B}$ receptors. The results in FIG. 10 suggest that (−)-trans-PAT is devoid of agonist activity at 5HT$_{2A}$ and 5HT$_{2B}$ receptors. Thus, pharmacological studies to assess antagonist activity were conducted, reported below.

Figure 13:
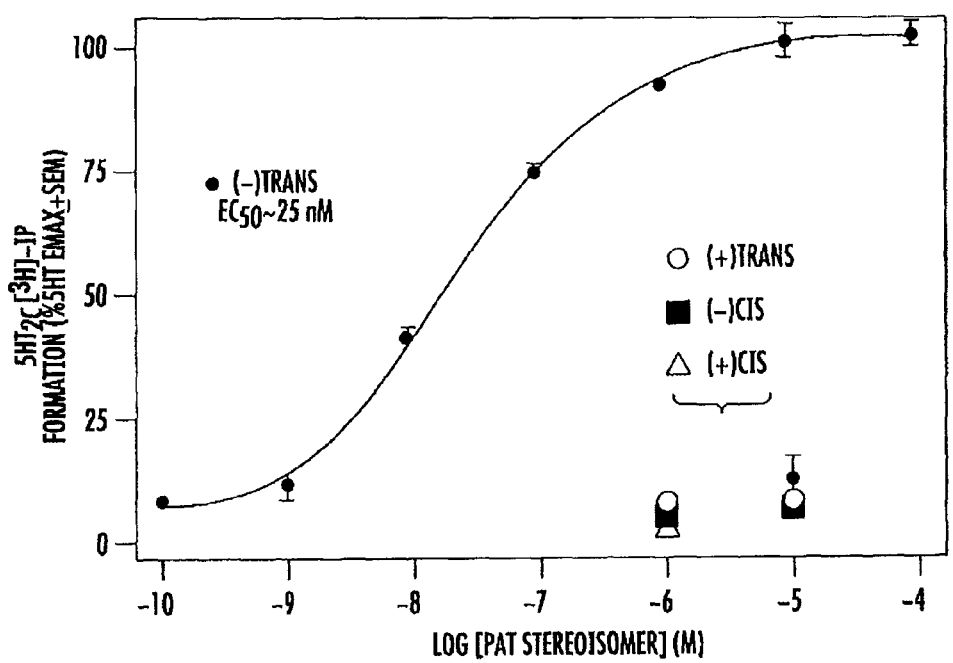
FIG. 13. (Example 10, 2(a) FIG. 10) depicts curves for inositol phosphates (IP) activity.
Figure 14:
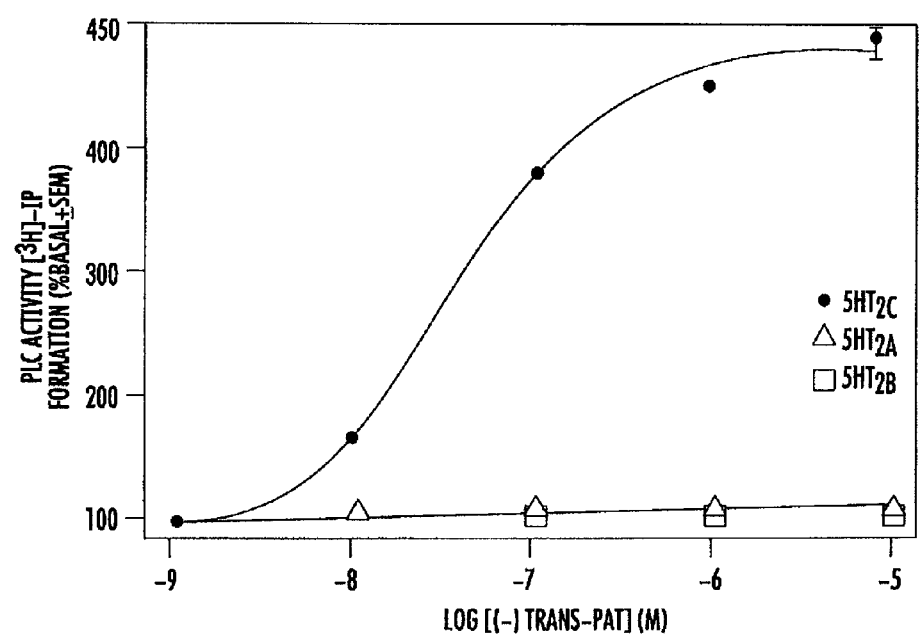
FIG. 14. (Example 10, 2(a) FIG. 11) depicts curves for PLC activity.
Figure 15:
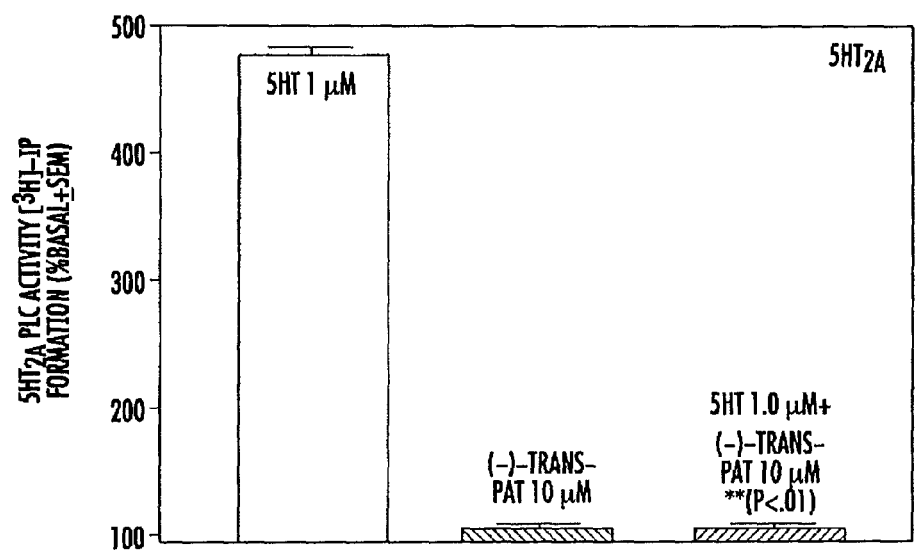
FIG. 15. (Example 10, 2(a) FIG. 12) depicts assessment for PLC activity.

2c. (−)-Trans-PAT is an Antagonist at 5HT$_{2A}$ and 5HT$_{2B}$ Receptors (FIGS. 12-13).

TABLE 5

| PAT Stereoisomer | 5HT$_{2A}$ Ki ± SEM | n$_H$ | 5HT$_{2B}$ Ki ± SEM | n$_H$ | 5HT$_{2C}$ Ki ± SEM | n$_H$ |
|---|---|---|---|---|---|---|
| (1R,3S)-(−)-trans-PAT | 407.3 ± 38.4 nM | 0.9 | 1,168.8 ± 6.3 nM | 1.0 | 37.6 ± 3.0 nM | 0.93 |
| (1S,3R)-(+)-trans-PAT | 520.1 ± 0.29 nM | 1.0 | ~2500 nM | 1.0 | 1270 ± 84.8 nM | 1.0 |
| (1S,3S)-(−)-cis-PAT | 1452.4 ± 0.23 nM | 1.0 | >5000 nM | | 433 ± 4.8 nM | 0.80 |
| (1R,3R)-(+)-cis-PAT | 776.8 ± 0.20 nM | 0.9 | >5000 nM | | 975 ± 7.8 nM | 0.76 |

Example 10

Figure 9:
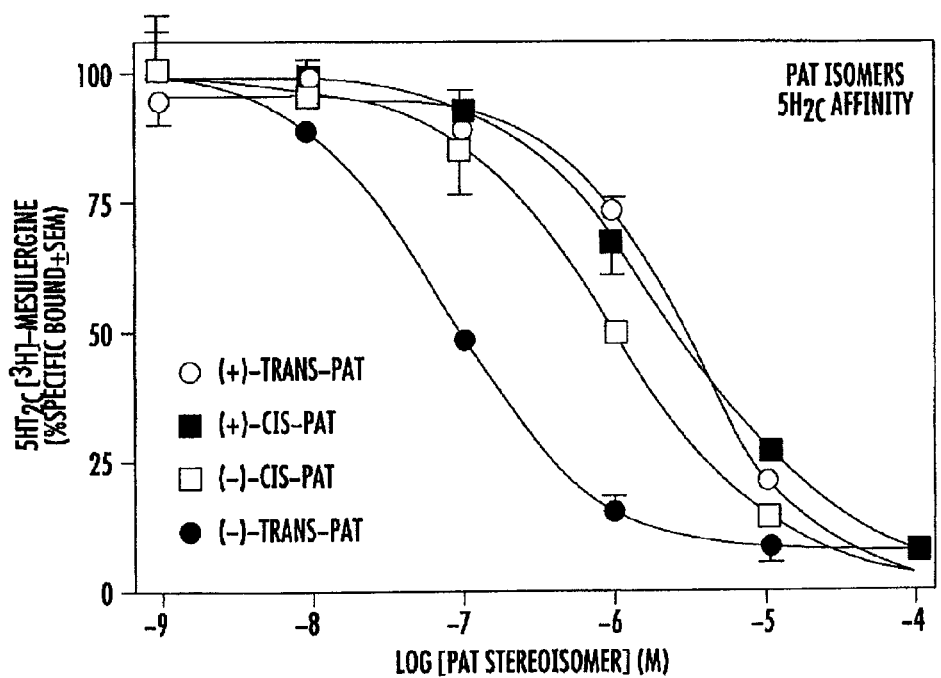
FIG. 9. (Example 9, 1(d) FIG. 5) depicts curves for 5-HT$_{2C}$ binding.

In Vitro Characterization of PAT Functional Activity at 5HT$_2$ Receptor Subtypes 2a. (−)-Trans-PAT is a Stereospecific Full Efficacy Agonist at 5HT$_{2C}$ Receptors (FIGS. 9-10).

Figure 8:
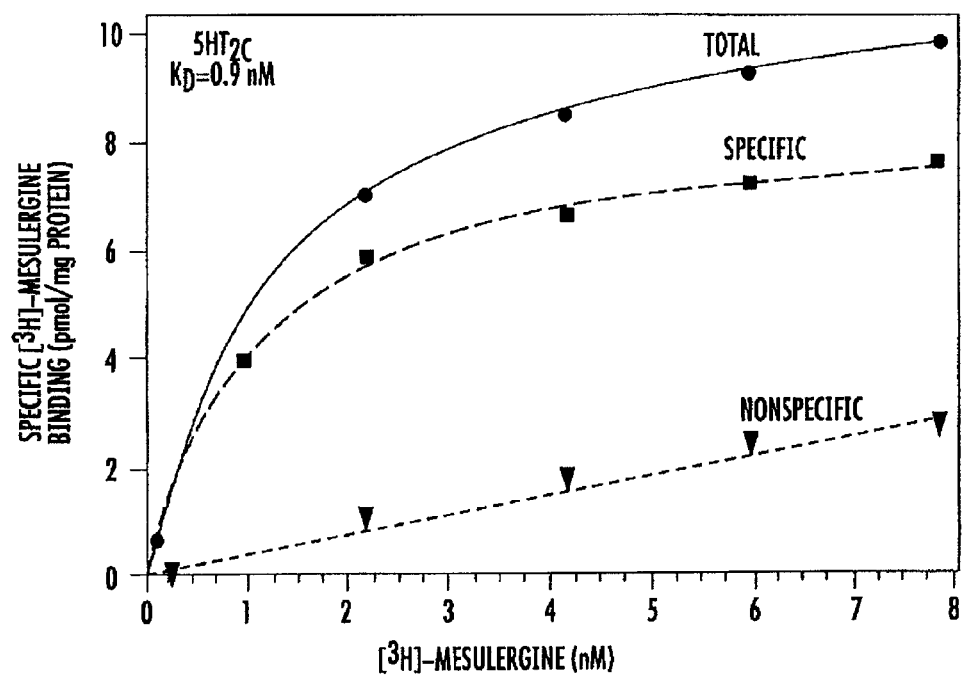
FIG. 8. (Example 9, 1(c) FIG. 4) depicts curves for 5-HT$_{2C}$ binding.

The 5HT$_2$ GPCRs are constitutively active and predominantly activate Gα$_q$ protein to stimulate phospholipase (PL) C and inositol phosphates (IP) formation in mammalian tissues (Raymond et al., 2001). FIG. 9 shows that in CHO-5HT$_{2C}$ cells, (−)-trans-PAT is a 5HT$_{2C}$ agonist (EC$_{50}$=21.4±2.22 nM, n$_H$=0.66) with full efficacy relative to 5HT (EC$_{50}$=6.30±0.55 nM, n$_H$=1.3) for stimulation of PLC/[$^3$H]-IP formation. FIG. 9 also shows that the APT analog Cl-6APT (5HT$_{2C}$ Ki~300 nM, FIG. 8), also is a full efficacy 5HT$_{2C}$ agonist, but, it has very low potency (EC$_{50}$=4,630±312 nM; n$_H$=0.63) in comparison to (−)-trans-PAT and 5HT.

The results for (−)-trans-PAT vs. Cl-6APT suggest that the position of the pendant phenyl ring is important, likely, for π-π stacking interactions with 5HT$_{2C}$ aromatic amino acids involved in receptor binding and/or activation. Mutational analysis of the 5-HT$_{2A}$ receptor suggests important ligand-receptor π-π binding interactions occur in TMDs 5 & 6.

At 5HT$_{2A}$ and 5HT$_{2B}$ receptors, (−)-trans-PAT is an antagonist of 5HT-mediated stimulation of PLC/IP formation (FIGS. 12, 13). At the 5HT$_{2B}$ receptor, we observed that (−)-trans-PAT at a concentration of 1.0 μM (about Ki, Table 5) did not achieve full blockade (not shown), likely, due to the comparatively high affinity of 5HT for the 5HT$_{2B}$ receptor (Ki~1.0 nM). At a (−)-trans-PAT concentration of 10 μM, however, 5HT (1.0 μM) did not surmount the blockade, suggesting a competitive antagonism. Experiments for full concentration-response curves to determine pA$_2$ values for (−)-trans-PAT at 5HT$_{2A}$ and 5HT$_{2B}$ receptors will be undertaken in our lab.

Example 11

Synthesis of Meta-Substituted PAT Analogs and Separation of Enantiomers (Schemes 1-3)

General Synthetic Methods:

Details are described in our synthetic medicinal chemistry publications (e.g., Ghoneim et al., 2006; Bucholtz et al., 1999; Wyrick et al., 1993; 1995). In vitro pharmacological studies initially will use racemic cis and trans products. Racemic PATs with Ki<50 nM will be resolved to (+)- and (−)- enantiomers by derivatization to the diastereomeric salt followed by differential crystallization or synthesized de novo using a chiral reduction step (Scheme 3). Absolute configuration is assigned by single crystal X-ray crystallography or spectrophotometric methods (NMR, optical rotation) by comparison to pure enantiomers already synthesized. Products (as HCl salts) characterized for purity using NMR, elemental analysis, mass spectrometry, melting point and thin layer chromatography.

Scheme 1: Meta-Substituted PATs:

Methods are modified from our papers cited above and others (Agarwal et al., 2005). The Claisen-Schmidt reaction using meta-substituted aldehyde 2 gives the α,β-unsaturated ketone 3, which is cyclized to the ketone 4 and reduced using NaBH$_4$. The (±)-cis and (±)-trans free base 7 is converted to the (1R)-(−)- or (1S)-(+)-camphor-10-sulfonic acid diastereomeric salt, which undergoes differential recrystallization to afford (+)- or

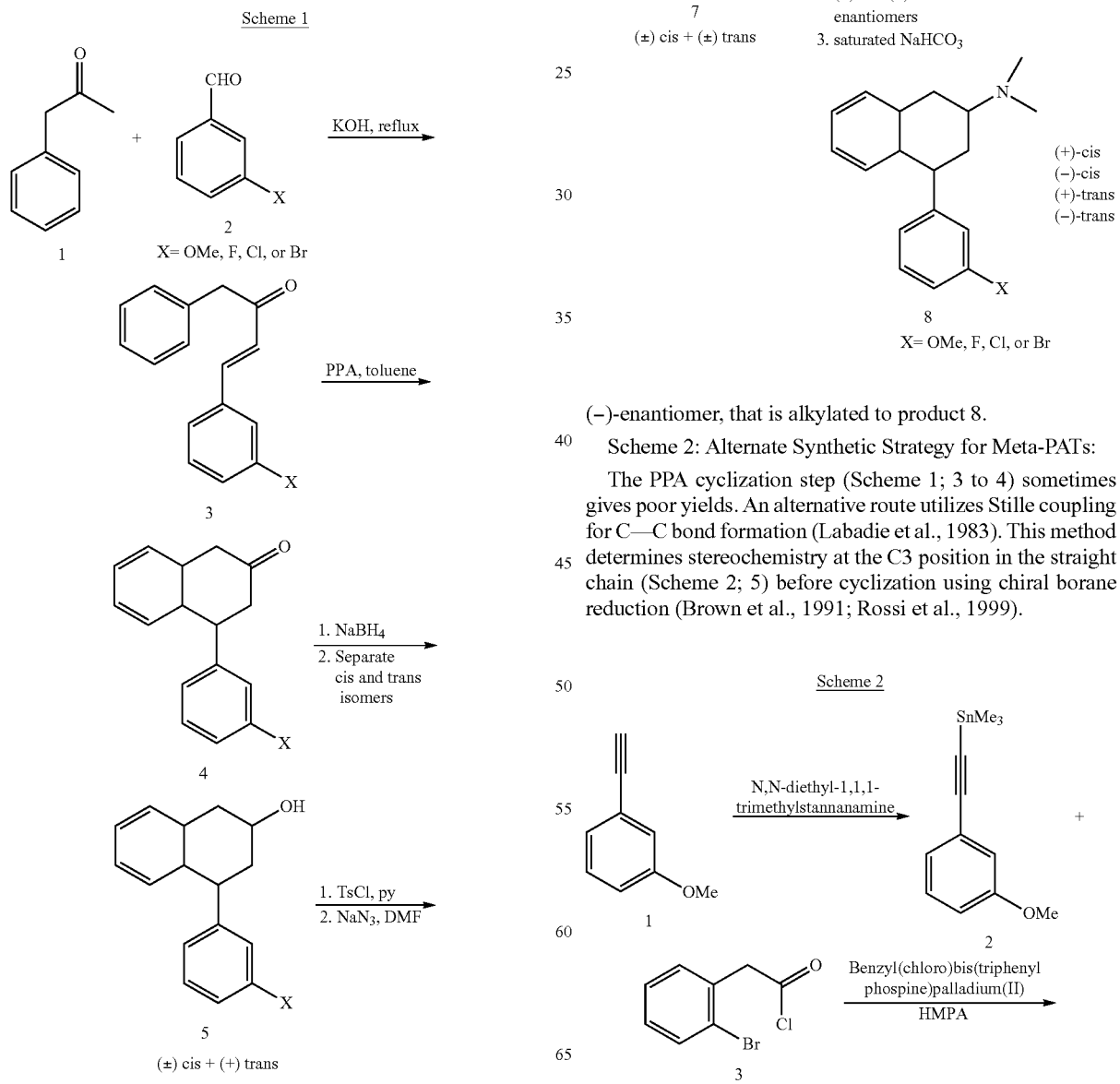

(−)-enantiomer, that is alkylated to product 8.

Scheme 2: Alternate Synthetic Strategy for Meta-PATs:

The PPA cyclization step (Scheme 1; 3 to 4) sometimes gives poor yields. An alternative route utilizes Stille coupling for C—C bond formation (Labadie et al., 1983). This method determines stereochemistry at the C3 position in the straight chain (Scheme 2; 5) before cyclization using chiral borane reduction (Brown et al., 1991; Rossi et al., 1999).

-continued

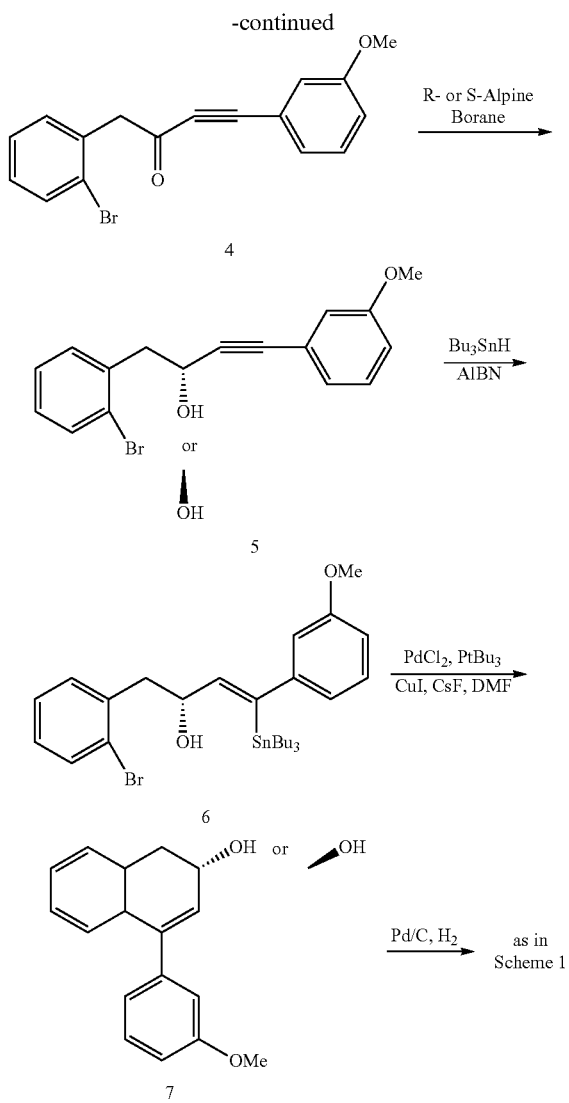

Scheme 3: Use of Chiral Reducing Agent to Obtain PAT Analog Stereoisomers: Di-isopinocamphenyl-borane (DIP) analogs recently were reported as stereoselective reducing agents for ketones with structures similar to the PAT ketone 4 in Scheme 3 (Cha et al., 2005).

2. Synthesis of PAT Analogs with Fixed Phenyl Ring (FIG. 16)

Figure 16:
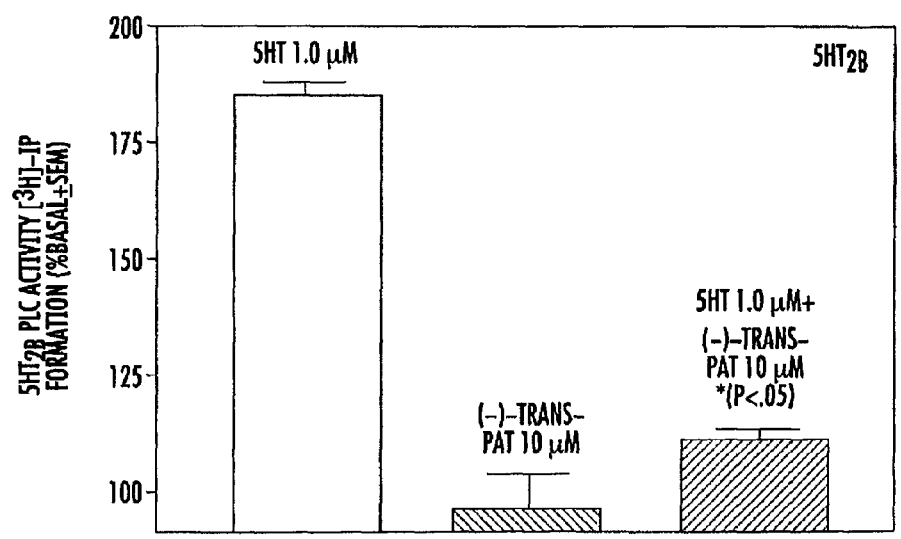
FIG. 16. (Example 10, 2(a) FIG. 13) depicts assessment for PLC activity.

The PAT pendant phenyl ring has a large degree of rotation flexibility relative to the tetrahydronapthalene scaffold, though it minimizes to a low energy orthogonal conformation. Analogous "pendant" phenyl ring systems are present in a fixed configuration in high affinity $5HT_{2C}$ antagonist ligands such as mesulergine and ketanserin, but not in any reported agonists. Fixing the PAT phenyl ring in an orthogonal configuration relative to the tetrahydronapthalene may enhance $5HT_{2C}$ affinity and provide information regarding PAT ligand-$5HT_{2C}$ receptor aromatic (π-π) binding interactions. We propose synthesis of the benzo[de]anthracene 1 and benzo[c]phenanthrene 2 rigid tetracyclic analogs with a slightly curved conformation. In addition, we propose synthesis of the spiroindane analog 3 wherein the phenyl ring is held at torsion angle 61°, similar to the X-ray crystal structure of (−)-trans-PAT (Wyrick et al., 1993); the related planar indane tetracyclic system in the tetrahydrofluoranthene analog 4 also will be synthesized.

i. 4,11-dihydro-5-N,N-dimethylamino-6H-benzo[de]anthracene (FIG. 16; 1)

Anthrone is subjected to a Wittig reaction to give the acetate (Spinella, 1997). After reduction of the alkene and ester group using NaBH$_4$ and PEG (Santaniello et al., 1981), the resultant alcohol is

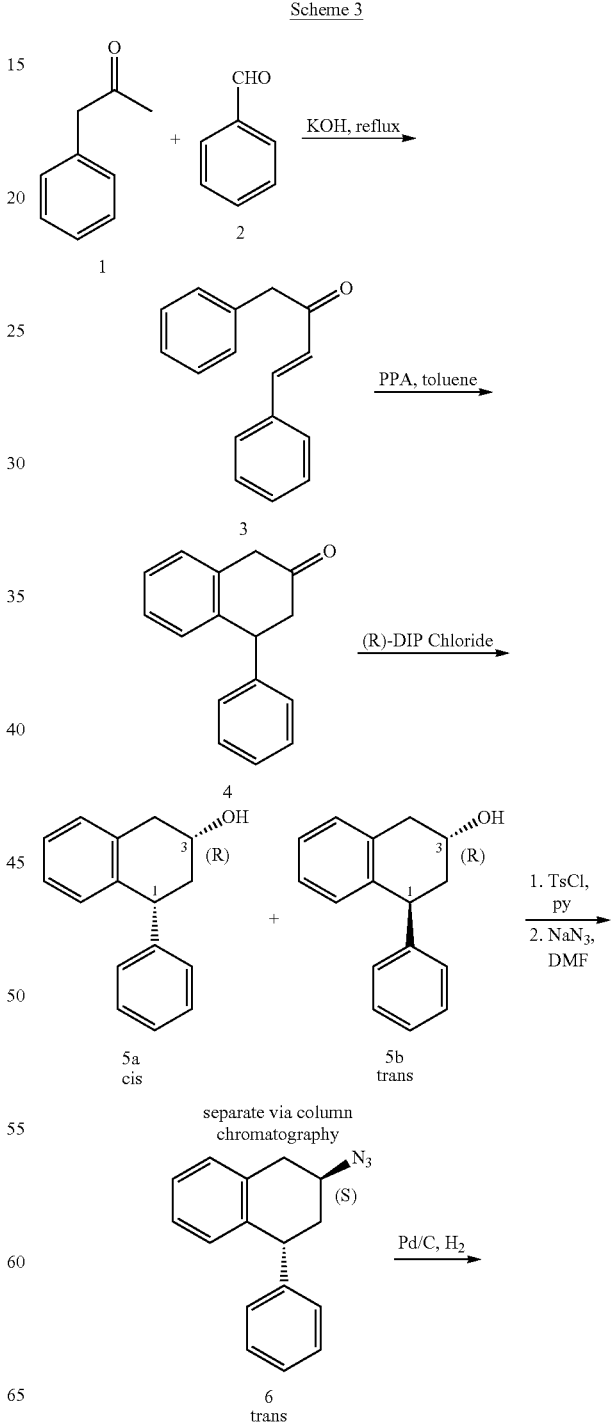

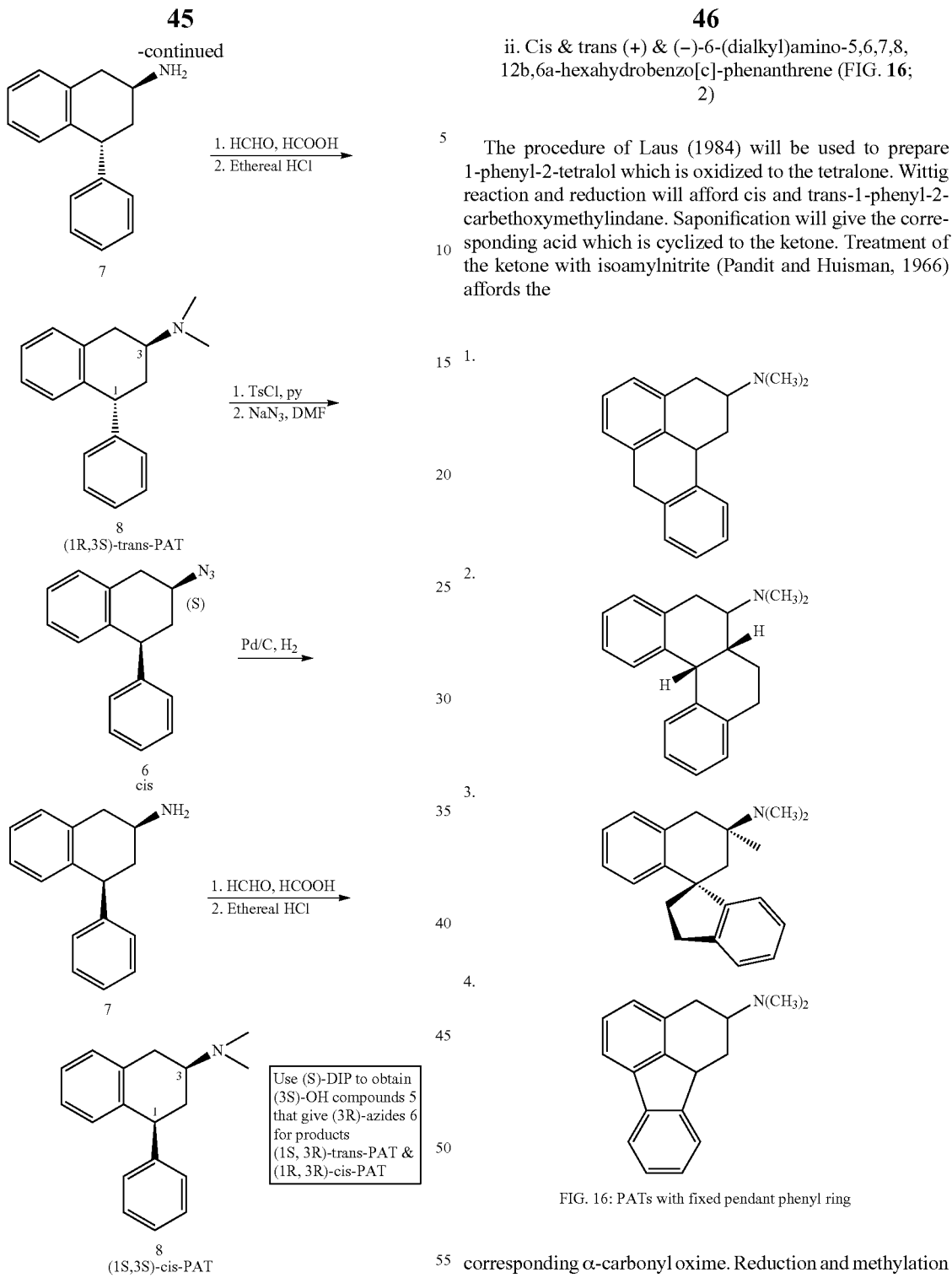

ii. Cis & trans (+) & (−)-6-(dialkyl)amino-5,6,7,8,12b,6a-hexahydrobenzo[c]-phenanthrene (FIG. 16; 2)

The procedure of Laus (1984) will be used to prepare 1-phenyl-2-tetralol which is oxidized to the tetralone. Wittig reaction and reduction will afford cis and trans-1-phenyl-2-carbethoxymethylindane. Saponification will give the corresponding acid which is cyclized to the ketone. Treatment of the ketone with isoamylnitrite (Pandit and Huisman, 1966) affords the FIG. 16: PATs with fixed pendant phenyl ring corresponding α-carbonyl oxime. Reduction and methylation give 2.

iii. Cis & trans (+) & (−)-3'(dialkyl)-aminospiro[indan-2,1(2'H)-3,4-dihydro-naphthalene] (FIG. 16; 3)

The procedure of Majerus (1967) is used to prepare bis(1-hydroxyindanyl) to 2-oxospiro[indan-2,1(2'H)-3,4-dihydronaphthalene. This ketone is treated with isoamyl nitrite to afford the α-oxime followed by reduction under acidic conditions to the cis and trans primary amines which are N,N-dialkylated to give product 3.

converted to 9-bromoethyl-10-hydroanthracene with hydrobromic acid. Reaction of the bromide with sodium cyanide is followed by hydrolysis to give the acid and Friedel Crafts ring closure will produce the ketone 5,11-dihydro-4-keto-6H-benzo[de]anthracene (Itoh et al., 1984) that undergoes the same reactions as the corresponding PAT ketone 4 in Scheme 3 to give 1 (FIG. 16).

iv. R- &
S-2-Dimethylamino-10b,1,2,3,tetrahydrofluoranthene
(FIG. 16; 4)

1-(Fluoren-9-yl)-propanoate is prepared by formylation of fluorene using potassium methoxide and ethyl formate followed by Wittig reaction to afford the olefin which will be catalytically reduced and the ester saponified according to the procedure of Von and Wagner (1944). This acid will be ring closed with PPA to afford 3-oxo-10b,1,2,3-tetrahydrofluoranthene. Reaction of this ketone with isoamyl nitrite to afford the α oxime followed by catalytic reduction to the primary amine and N,N-alkylation to product 4 (FIG. 16).

Synthesis of New PAT Analogs with Changes to the C(1) Pendant Phenyl Substituent Based on binding, function, 3D QSAR, and molecular modeling results in Preliminary Data, we hypothesize the (−)-trans-PAT C(1) pendant phenyl moiety is critical to providing full-efficacy $5HT_{2C}$ agonist activity without activation of $5HT_{2A}$ and $5HT_{2B}$ receptors. Testing PAT pendant phenyl ring substitution and orientation will help to determine optimal steric and electrostatic binding interactions with $5HT_2$ active site amino acids to obtain $5HT_{2C}$ agonists and/or $5HT_{2A}/5HT_{2B}$ antagonists with higher affinity, potency, and/or selectivity.

benzene ruthenium (II) chloride dimer and the chiral ligand (R,R)-N-(2-amino-1,2-diphenylethyl)-p-toluenesulfonamide ((R,R)-NAPTS) to give the (R)-β-tetralol (2) (Mogi et al., 2004). In Step B, the (R)-β-tetralol (2) is converted to the tert-butyldimethylsilyl (TBDMS) derivative (3) (TBDMS protecting group to prevent bromination at adjacent benzylic position). In Step C, the TBDMS protected compound is brominated with N-Bromosuccinimide (Agarwal et al., 1990) under reflux in anhydrous $CCl_4$ to give the brominated common intermediate (4), separated to cis and trans bromo compounds by flash column chromatography. In Step D, each (cis and trans) brominated intermediate (4) is reacted with commercially available boronic acids ($R_2B(OH)_2$, $R_2$=a-p in Chart 1) under a Nickel-Catalyzed Suzuki

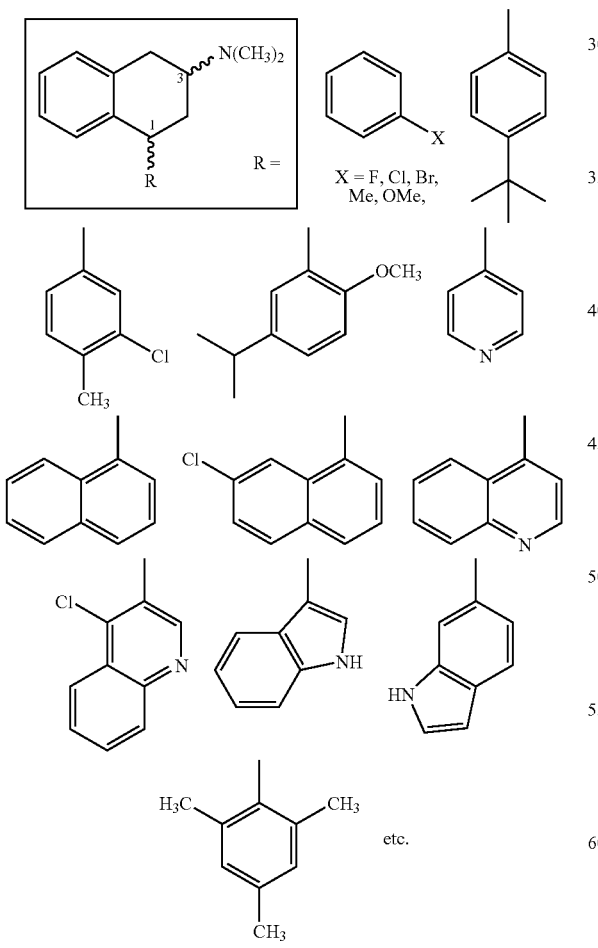

Chart of New C(1) Substituted PAT Analogs

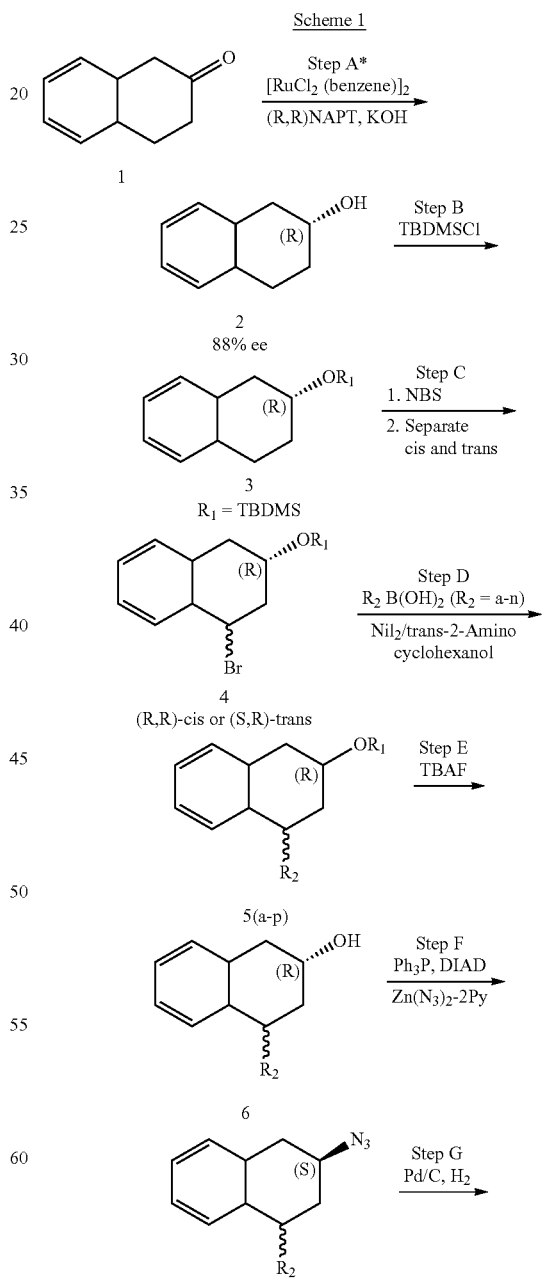

Scheme 1 shows the synthetic strategy for the new PATs in the Chart above. In Step A, β-tetralone (1) is refluxed with

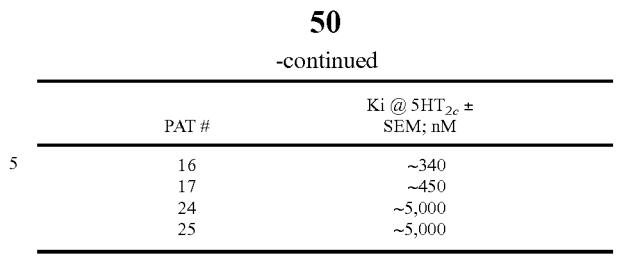

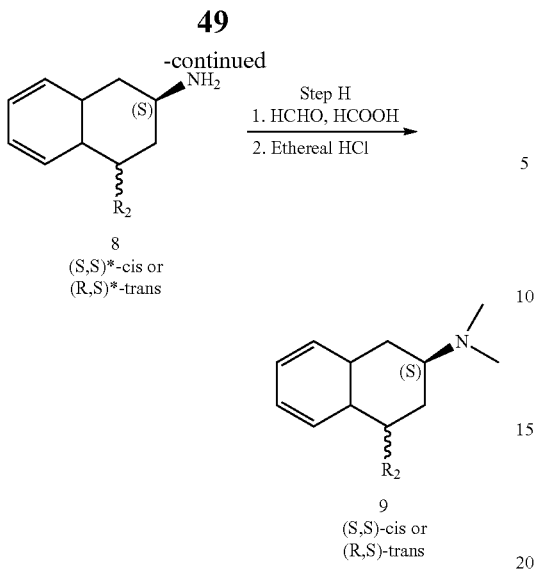

reaction (Gonzalez-Bobes et al) using NiI$_2$/trans-2-aminocyclohexanol with sodium bis(trimethylsilyl)amide under reflux to make the various cis and trans PAT analogs 50(a-p) shown in Table 2. In Step E, the TBDMS protected PAT analogs are deprotected using tetrabutylammonium fluoride (TBAF) in tetrahydrofuran. In Step F, the cis and trans hydroxyl PAT analogs are converted in one-pot to the corresponding trans and cis azido PAT intermediates (7) using a Mitsunobu reaction with zinc azide/bis-pyridine complex, diisopropyl azodicarboxylate (DIAD) and triphenylphosphene (Vorogushin et al., 2003). In Step G, the azido PAT derivatives are reduced to the corresponding PAT amines (8). In Step H, these enantiomeric cis and trans amines are converted to the dimethylated PAT analogs using Eschweiler-Clarke methylation with formic acid/formaldehyde under reflux. Racemic PATs with Ki<50 nM will be resolved to (+)- and (−)-enantiomers by derivatization of the un-methylated free amine to the diastereomeric salt followed by differential crystallization or synthesized de novo using a chiral reduction step. Absolute configuration is assigned by single crystal X-ray crystallography or spectrophotometric methods (NMR, optical rotation) by comparison to pure enantiomers already synthesized. Products (as HCl salts) characterized for purity using NMR, elemental analysis, mass spectrometry, melting point and thin layer chromatography.

Example 12

Affinity for 5-HT2c: representative compound results

| PAT # | Ki @ 5HT$_{2c}$ ± SEM; nM |
|---|---|
| 1 | 37.6 ± 3.00 |
| 2 | 1270 ± 84.8 |
| 3 | 430 ± 4.8 |
| 4 | 980 ± 7.812 |
| 5 | ~1800 |
| 6 | ~1200 |
| 7 | 20.0 ± 1.10 |
| 8 | ~250 |
| 9 | ~300 |
| 10 | ~5,000 |
| 13 | 200 |
| 14 | ~300 |
| 15 | ~170 |
| 16 | ~340 |
| 17 | ~450 |
| 24 | ~5,000 |
| 25 | ~5,000 |

Example 13

Muscarinic Receptor Activity of Compounds of the Invention

Muscarinic receptor activity is assessed using any suitable protocol, including those essentially as described in: Novascreen, NIMH Psychotherapeutic Drug Discovery and Development Program, Oceanix Biosciences Corporation, 1996; and PDSP, Psychoactive Drug Screening Program; B L Roth, Director. NIMH Contract NO2MH80002, Case Western Reserve University, Cleveland, Ohio, and University of North Carolina, Chapel Hill, N.C., 2005.

| Muscarinic Receptor Activity of PAT | |
|---|---|
| Muscarinic Receptor | Affinity of (+/−)trans-PAT Ki (nM) |
| M1 | 2400 |
| M2 | |
| M3 | 1300 |
| M4 | |
| M5 | 600 |

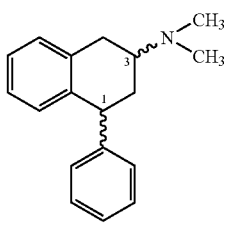 [SMILES: CN(C)C1Cc2ccccc2C(c2ccccc2)C1]

REFERENCES

Arjona A A, Pooler A M, Lee R K, Wurtman R J. Effect of a 5-HT$_{2C}$ serotonin agonist, dexnorfenfluramine, on amyloid precursor protein metabolism in guinea pigs. Brain Res. 2002 951:135-140.

Baldessarini R J, Tarazi F I. Pharmacotherapy of Psychosis and mania. In: Brunton L L, Laxo J S, Parker K L, eds. The Pharmacological Basis of Therapeutics. 11th ed. New York: McGraw-Hill, 2006: 461-500.

Bubar M J, Cunningham K A. Distribution of serotonin 5-HT (2C) receptors in the ventral tegmental area. Neuroscience. 2007 (doi: 10.1016/j.neuroscience.2006.12.071).

Bubar M J, Cunningham K A. Serotonin 5-HT2A and 5-HT2C receptors as potential targets for modulation of psychostimulant use and dependence. Current Topics and Medicinal Chemistry 2006; 6:1971-1985.

Connolly H M, Crary J L, McGoon M D, Hensrud D D, Edwards B S, Edwards W D, Schaff H V. Valvular heart disease associated with fenfluramine-phentermine. N Engl J Med. 1997; 337:581-5888. Erratum in: N Engl J Med 1997; 337:1783.

Fitzgerald L W, Burn T C, Brown B S, Patterson J P, Corjay M H, Valentine P A, Sun J H, Link J R, Abbaszade I, Hollis J M, et al. Possible role of valvular serotonin 5-HT(2B) receptors in the cardiopathy associated with fenfluramine. Mol Pharmacol 2000 57: 75-81.

Fletcher P J, Grottick A J, Higgins G A. Differential effects of the 5-HT(2A) receptor antagonist M100907 and the 5-HT(2C) receptor antagonist SB242084 on cocaine-induced locomotor activity, cocaine self-administration and cocaine-induced reinstatement of responding. Neuropsychopharmacology 2002 27:576-586.

Frank M G, Stryker M P, Tecott L H. Sleep and sleep homeostasis in mice lacking the 5-HT2c receptor. Neuropsychopharmacology. 2002 27:869-873.

Ghoneim et al., Bioorg. Med. Chem., 14, 6640-6658 (2006).

Giorgetti M, Tecott L H. Contributions of 5-HT(2C) receptors to multiple actions of central serotonin systems. Eur J Pharmacol. 2004 488:1-9.

Heisler L K, Chu H M, Tecott L H. Epilepsy and obesity in serotonin 5-HT2C receptor mutant mice. Ann N Y Acad Sci. 1998 861:74-78.

Heisler L K, Cowley M A, Tecott L H, Fan W, Low M J, Smart J L, Rubinstein M, Tatro J B, Marcus J N, Holstege H, et al. Activation of central melanocortin pathways by fenfluramine. Science (Wash D.C.) 2002 297: 609-611.

Heisler L K, Tecott L H. A paradoxical locomotor response in serotonin 5-HT(2C) receptor mutant mice. J Neurosci. 2000 20:RC71.

Heisler L K, Zhou L, Bajwa P, Hsu J, Tecott L H Serotonin 5-HT(2C) receptors regulate anxiety-like behavior. Genes Brain Behav. 2007 (DOI 10.1111/j.1601-183X.2007.00316.x)

Jensen M D. Potential role of new therapies in modifying cardiovascular risk in overweight patients with metabolic risk factors. Obesity. 2006 14:143S-149S.

Julius D, Huang K N, Livelli T J, Axel R, Jessel T M. The 5HT2 receptor defines a family of structurally distinct but functionally conserved serotonin receptors. Proc. Natl. Acad. Sci. 1990 87:928-932.

Julius D, MacDermott A B, Axel R, Jessell T M. Molecular Characterization of a functional cDNA encoding the serotonin 1c receptor. Science 1988 241:558-564.

Kennett G A, Pittaway K, Blackburn T P: Evidence that 5-HT2C receptor antagonists are anxiolytic in the rat Geller-Seifter model of anxiety. *Psychopharmacology (Berl.)* (1994) 114:90-96.

Launay J M, Herve P, Peoc'h K, Tournois C, Callebert J, Nebigil C G, Etienne N, Drouet L, Humbert M, Simonneau G, et al. Function of the serotonin 5-hydroxytryptamine 2B receptor in pulmonary hypertension. Nat Med 2002 8: 1129-1135.

Marquis K L, Sabb A L, Logue S F, Brennan J A, Piesla M J, Comery T A, Grauer S M, Ashby C R Jr, Nguyen H Q, Dawson L A, Barrett J E, Stack G, Meltzer H Y, Harrison B L, Rosenzweig-Lipson S. WAY-163909 [(7bR,10aR)-1,2,3,4,8,9,10,10a-octahydro-7bH-cyclopenta-[b][1,4]diazepino[6,7,1hi]indole]: A novel 5-hydroxytryptamine 2C receptor-selective agonist with preclinical antipsychotic-like activity. J Pharmacol Exp Ther. 2007 320:486-496.

Muller C P, Huston J P. Determining the region-specific contributions of 5-HT receptors to the psychostimulant effects of cocaine. Trends Pharmacol Sci. 2006 27:105-112.

Nichols D E. Hallucinogens, Pharmacol. Ther. 2004 101:131-181.

Nilsson B M. 5-Hydroxytryptamine 2C (5-HT2C) receptor agonists as potential antiobesity agents. J Med Chem. 2006 49:4023-4034.

Palvimaki E P, Roth B L, Majasuo H, Laakso A, Kuoppamaki M, Syvalahti E, Hietala J. Interactions of selective serotonin reuptake inhibitors with the serotonin 5-HT2c receptor. psychopharmacology (Berl). 1996 126:234-240.

Pouwels H M, Smeets J L, Cheriex E C, Wouters E F. Pulmonary hypertension and fenfluramine. Eur Respir J. 1990 May; 3(5):606-7.

Raymond J R. Mukhin Y V. Gelasco A. Turner J. Collinsworth G. Gettys T W. Grewal J S. Garnovskaya M N. Multiplicity of mechanisms of serotonin receptor signal transduction. Pharmacol Ther. 2001 92:179-212.

Reynolds G P, Yao Z, Zhang X, Sun J, Zhang Z. Pharmacogenetics of treatment in first-episode schizophrenia: D3 and 5-HT2C receptor polymorphisms separately associate with positive and negative symptom response. Eur Neuropsychopharmacol. 2005 March; 15(2):143-51.

Rocha B A, Goulding E H, O'Dell L E, Mead A N, Coufal N G, Parsons L H, Tecott L H. Enhanced locomotor, reinforcing, and neurochemical effects of cocaine in serotonin 5-hydroxytryptamine 2C receptor mutant mice. J Neurosci. 2002; 22:10039-10045.

Rosenzweig-Lipson S, Sabb A, Stack G, Mitchell P, Lucki I, Malberg J E, Grauer S, Brennan J, Cryan J F, Sukoff Rizzo S J, Dunlop J, Barrett J E, Marquis K L. Antidepressant-like effects of the novel, selective, 5-HT(2C) receptor agonist WAY-163909 in rodents. Psychopharmacology (Berl). 2007 192:159-170.

Roth B L. Drugs and valvular heart disease. N Engl J Med. 2007; 356:6-9.

Rothman R B, Baumann M H, Savage J E, Rauser L, McBride A, Hufeisen S J, and Roth B L. Evidence for possible involvement of 5-HT(2B) receptors in the cardiac valvulopathy associated with fenfluramine and other serotonergic medications. Circulation 2000 102: 2836-2841.

Saltzman A G, Morse B, Whitman M M, Ivanshchenko Y, Jaye M, Felder S. Cloning of the human serotonin 5-HT2 and 5-HT1C receptor subtypes. Biochem Biophys Res Commun. 1991 181:1469-7148.

Sanders-Bush E, Mayer S E. Serotonin Receptor Agonists and Antagonists. Chapter 11, in Goodman and Gilman's The Pharmacological Basis of Therapeutics 11$^{th}$ Edition. Brunton L L, Lazo J S, Parker K L, Editors, McGraw-Hill, New York, 297-315, 2006.

Sard H, Kumaran G, Morency C, Roth B L, Toth B A, He P, Shuster L. SAR of psilocybin analogs: discovery of a selective 5-HT 2C agonist. Bioorg Med Chem Lett. 2005 15:4555-4559.

Segman R H, Heresco-levy U, Finkel B, Inbar R, Neeman T, Schlafman M, Dorevitch A, Yakir A, Lerner A, Goltser T, Shelevoy A, Lerer B. Association between the serotonin 2C receptor gene and tardive dyskinesia in chronic schizophrenia: additive contribution of 5-HT2CSer and DRD3Gly alleles to susceptibility, Psychopharmacology 2000 152:408-413.

Setola V, Dukat M, Glennon R A, Roth B L. Molecular determinants for the interaction of the valvulopathic anorexigen norfenfluramine with the 5-HT$_{2B}$ receptor. Mol Pharmacol 2005 68:20-33.

Simansky K J. NIH symposium series: ingestive mechanisms in obesity, substance abuse and mental disorders. Physiology & Behavior 2005; 86: 1-4.

Siuciak J A, Chapin D S, McCarthy S A, Guanowsky V, Brown J, Chiang P, Marala R, Patterson T, Seymour P A, Swick A, Iredale P A. CP-809,101, a selective 5-HT2C agonist, shows activity in animal models of antipsychotic activity. Neuropharmacology. 2007 52:279-290.

Smith S R, Prosser W, Donahue D, Anderson C, Shanahan W. Lorcaserin Phase 2b Clinical Study. American Diabetes Association, 2006.

Stein T D, Anders N J, DeCarli C, Chan S L, Mattson M P, Johnson J A. Neutralization of transthyretin reverses the neuroprotective effects of secreted amyloid precursor protein (APP) in $APP_{Sw}$ mice resulting in tau phosphorylation and loss of hippocampal neurons: support for the amyloid hypothesis. J. Neurosci. 2004 24:7707-7717.

Tecott L H, Sun L M, Akana S F, Strack A M, Lowenstein D H, Dallman M F, Julius D. Eating disorder and epilepsy in mice lacking 5-HT2c serotonin receptors. Nature. 1995 374:542-546

Tohda M, Takasu T, Nomura Y. Effects of antidepressants on serotonin-evoked current in *Xenopus oocytes* injected with rat brain mRNA. Eur J Pharmacol. 1989 166:57-63.

Veenstra-VanderWeele J, G. M. Anderson G M, Cook E H. Pharmacogenetics and the serotonin system: initial studies and future directions. Eur. J. Pharmacol. 2000 410:65-181.

Vickers S P, Dourish C T, and Kennett G A. Evidence that hypophagia induced by D-fenfluramine and D-norfenfluramine in the rat is mediated by 5-HT2C receptors. Neuropharmacology 2001 41: 200-209.

Vickers, S. P., Clifton, P. G., Dourish, C. T. and Tecott, L. H., 1999. Reduced satiating effect of d-fenfluramine in serotonin 5-HT2C receptor mutant mice. Psychopharmacology 1999 143:309-314.

Agarwal R, Boyd D R, McMordie R A S, O'Kane G A, Porter P, Sharma N D, Dalton H, Gray D J. J. Chiral arene hydrates of naphthalene: Enzymatic and chemical syntheses. Chem Soc Chem Commun. 1990 1711-1713.

Mogi M, Fugi K, Node M. Asymmetric reduction of methoxy substituted β-tetralones using hydrogenation. Tetrahedron: Asymmetry. 2004 15:3715-3717.

Vorogushin A V, Predeus A, Wuff W D, Hansen H. Diels-Alder reaction-aromatization approach toward functionalized ring C allocolchicinoids. Enantioselective total synthesis of (−)-7S-Allocolchicine. J Org Chem.

The recitation of a listing of elements in any definition of a variable herein includes definitions of that variable as any single element or combination of listed elements. The recitation of an element, or an embodiment herein includes that element or embodiment as any single element or embodiment or in combination with any other element, embodiments or portions thereof.

All references cited herein, whether in print, electronic, computer readable storage media or other form, are expressly incorporated by reference in their entirety, including but not limited to, abstracts, articles, journals, publications, texts, treatises, technical data sheets, internet web sites, databases, patents, patent applications, and patent publications.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A method of treating a GPCR-mediated disorder in a subject comprising administering to the subject identified as in need thereof a compound, wherein the GPCR-mediated disorder is selected from a neuropsychiatric disorder, a neurodegenerative disorder, a neurological disorder, a cardiovascular disorder, a gastrointestinal disorder, or a genito-urinary tract disorder; and the compound is:

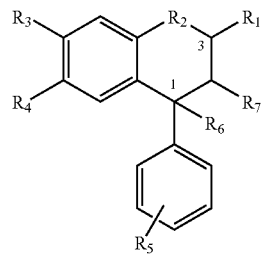

wherein,
$R_1$ is independently H, $NH_2$, NH(alkyl), $N(alkyl)_2$;
$R_2$ is independently —$(CH_2)n$-;
Each n is independently 1 or 2;
$R_3$ is independently H, OH, or halo;
$R_4$ is independently H, OH, or halo;
$R_5$ is alkyl or halo;
$R_6$ is independently H or alkyl;
$R_7$ independently H, $N(alkyl)_2$;
the neuropsychiatric disorder is selected from the group consisting of obesity, addiction, anxiety, depression, schizophrenia, and sleep disorders;
the neurodegenerative disorder is selected from the group consisting of Parkinson's Disease and Alzheimer's Disease;
the neurological disorder is epilepsy;
the cardiovascular disorder is hypertension;
the gastrointestinal disorder is irritable bowel syndrome; and
the genito-urinary tract disorder is bladder control.

2. The method of claim 1, wherein the compound is a compound of the following table:

| Config | $R_1$ | $R_2$ | $R_3$ | $R_4$ | $R_5$ | $R_6$ | $R_7$ |
|---|---|---|---|---|---|---|---|
| (±)-trans | $N(CH_3)_2$ | $CH_2$ | H | H | p-Cl | H | H |
| (±)-trans | $N(CH_3)_2$ | $CH_2$ | H | H | p-F | H | H |
| (±)-trans | $N(CH_3)_2$ | $CH_2$ | H | H | p-$CH_3$ | H | H |
| (±)-trans | $N(CH_3)_2$ | $CH_2$ | H | H | o-Cl | H | H |
| (±)-trans | $N(CH_3)_2$ | $CH_2$ | H | H | o-$CH_3$ | H | H |
| (±)-trans | $N(CH_3)_2$ | $CH_2$ | H | H | m-$OCH_3$ | H | H |
| (±)-trans | $N(CH_3)_2$ | $CH_2$ | H | H | m-F | H | H |
| (±)-trans | $N(CH_3)_2$ | $CH_2$ | H | H | m-Cl | H | H |
| (±)-trans | $N(CH_3)_2$ | $CH_2$ | H | H | m-Br | H | H |
| (±)-trans | $N(CH_3)_2$ | $CH_2$ | H | H | m-$CH_3$ | H | H |
| (±)-trans | $N(CH_3)_2$ | $CH_2$ | H | H | p-$C(CH_3)_3$ | H | H. |

3. The method of claim 1, wherein in the compound $R_1$ is —$NMe_2$.

4. The method of claim 3, wherein the-compound is (1R, 3S)-(−)-Trans-1-(3-bromo-phenyl-3-N,N-dimethylamino-1,2,3,4-tetrahydronaphthalene.

5. The method of claim 1, wherein the disorder is cocaine addiction.

6. The method of claim 1, wherein the disorder is obesity.

7. A method of treating a GPCR-mediated disorder in a subject comprising administering to the subject identified as in need thereof a compound, wherein the GPCR-mediated disorder is selected from a neuropsychiatric disorder, a neurodegenerative disorder, a neurological disorder, a cardiovascular disorder, a gastrointestinal disorder, or a genito-urinary tract disorder; and the compound is:

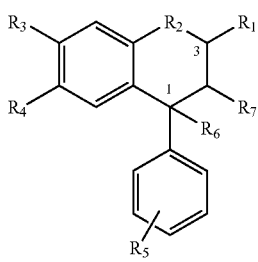

wherein,
R$_1$ is independently H, NH$_2$, NH(alkyl), N(alkyl)$_2$;
R$_2$ is independently —(CH$_2$)n-;
Each n is independently 1 or 2;
R$_3$ is independently OH or halo;
R$_4$ is independently H, OH, or halo;
R$_5$ is H;
R$_6$ is independently H or alkyl;
R$_7$ independently H, N(alkyl)$_2$;
the neuropsychiatric disorder is selected from the group consisting of obesity, addiction, anxiety, depression, schizophrenia, and sleep disorders;
the neurodegenerative disorder is selected from the group consisting of Parkinson's Disease and Alzheimer's Disease;
the neurological disorder is epilepsy;
the cardiovascular disorder is hypertension;
the gastrointestinal disorder is irritable bowel syndrome; and
the genito-urinary tract disorder is bladder control.

8. The method of claim 7, wherein the compound is a compound of the following table:

| Config | R$_1$ | R$_2$ | R$_3$ | R$_4$ | R$_5$ | R$_6$ | R$_7$ |
|---|---|---|---|---|---|---|---|
| (±)-trans | N(CH$_3$)$_2$ | CH$_2$ | Cl | OH | H | H | H |
| (±)-cis | N(CH$_3$)$_2$ | CH$_2$ | Cl | OH | H | H | H |
| (±)-trans | N(CH$_3$)$_2$ | CH$_2$ | OH | OH | H | H | H |
| (±)-cis | N(CH$_3$)$_2$ | CH$_2$ | OH | OH | H | H | H |
| (±)-trans | NH$_2$ | CH$_2$ | OH | OH | H | H | H |
| (±)-cis | NH$_2$ | CH$_2$ | OH | OH | H | H | H. |

9. A method of treating a GPCR-mediated disorder in a subject comprising administering to the subject identified as in need thereof a compound, wherein the GPCR-mediated disorder is selected from a neuropsychiatric disorder, a neurodegenerative disorder, a neurological disorder, a cardiovascular disorder, a gastrointestinal disorder, or a genito-urinary tract disorder; and the compound is:

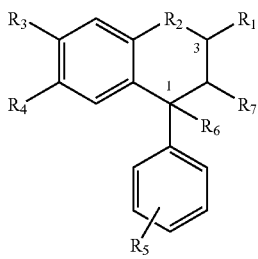

wherein,
R$_1$ is independently H, NH$_2$, NH(alkyl), N(alkyl)$_2$;
R$_2$ is independently —(CH$_2$)n-;
Each n is independently 1 or 2;
R$_3$ is independently H, OH, or halo;
R$_4$ is independently OH or halo;
R$_5$ is H;
R$_6$ is independently H or alkyl;
R$_7$ independently H, N(alkyl)$_2$;
the neuropsychiatric disorder is selected from the group consisting of obesity, addiction, anxiety, depression, schizophrenia, and sleep disorders;
the neurodegenerative disorder is selected from the group consisting of Parkinson's Disease and Alzheimer's Disease;
the neurological disorder is epilepsy;
the cardiovascular disorder is hypertension;
the gastrointestinal disorder is irritable bowel syndrome; and
the genito-urinary tract disorder is bladder control.

10. The method of claim 3, wherein the compound is (−)-(trans)-4-(4-chlorophenyl)-N,N-dimethyl-1,2,3,4-tetrahydronaphthalen-2-amine, (−)-(trans)-4-(4-fluorophenyl)-N,N-dimethyl-1,2,3,4-tetrahydronaphthalen-2-amine, (−)-(trans)-4-(4-methylphenyl)-N,N-dimethyl-1,2,3,4-tetrahydronaphthalen-2-amine, or (−)-(trans)-4-(2-chlorophenyl)-N,N-dimethyl-1,2,3,4-tetrahydronaphthalen-2-amine.

11. A method of treating a GPCR-mediated disorder in a subject comprising administering to the subject identified as in need thereof a compound, wherein the GPCR-mediated disorder is selected from a neuropsychiatric disorder, a neurodegenerative disorder, a neurological disorder, a cardiovascular disorder, a gastrointestinal disorder, or a genito-urinary tract disorder; and the compound is:

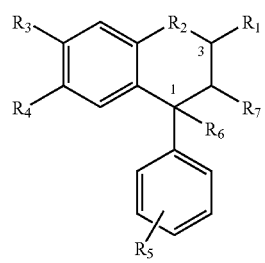

wherein,
R$_1$ is independently N(C$_2$H$_5$)$_2$, N(C$_3$H$_5$)$_2$, NCH$_3$(C$_3$H$_5$), or NH(C$_3$H$_5$);
R$_2$ is independently —(CH$_2$)n-;
Each n is independently 1 or 2;
R$_3$ is independently H, OH, or halo;
R$_4$ is independently H, OH or halo;
R$_5$ is H;
R$_6$ is independently H or alkyl;
R$_7$ independently H, N(alkyl)$_2$;
the neuropsychiatric disorder is selected from the group consisting of obesity, addiction, anxiety, depression, schizophrenia, and sleep disorders;
the neurodegenerative disorder is selected from the group consisting of Parkinson's Disease and Alzheimer's Disease;
the neurological disorder is epilepsy;
the cardiovascular disorder is hypertension;
the gastrointestinal disorder is irritable bowel syndrome; and
the genito-urinary tract disorder is bladder control.

12. The method of claim 11, wherein the compound is a compound of the following table:

| Config | $R_1$ | $R_2$ | $R_3$ | $R_4$ | $R_5$ | $R_6$ | $R_7$ |
|---|---|---|---|---|---|---|---|
| (±)-trans | $N(C_2H_5)_2$ | $CH_2$ | H | H | H | H | H |
| (±)-trans | $N(C_3H_5)_2$ | $CH_2$ | H | H | H | H | H |
| (±)-trans | $NCH_3(C_3H_5)$ | $CH_2$ | H | H | H | H | H |
| (±)-trans | $NH(C_3H_5)$ | $CH_2$ | H | H | H | H | H. |

\* \* \* \* \*